US012661412B2

(12) United States Patent
Esteves et al.

(10) Patent No.: US 12,661,412 B2
(45) Date of Patent: *Jun. 23, 2026

(54) METHOD TO ENHANCE THE EFFICIENCY OF SYSTEMIC AAV GENE DELIVERY TO THE CENTRAL NERVOUS SYSTEM

(71) Applicant: University of Massachusetts, Westborough, MA (US)

(72) Inventors: Miguel Sena Esteves, Worcester, MA (US); Ana Rita Batista, Worcester, MA (US); Sourav Roy Choudhury, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 176 days.

This patent is subject to a terminal disclaimer.

(21) Appl. No.: 18/490,841

(22) Filed: Oct. 20, 2023

(65) Prior Publication Data

US 2024/0139340 A1 May 2, 2024

Related U.S. Application Data

(63) Continuation of application No. 16/074,968, filed as application No. PCT/US2017/016194 on Feb. 2, 2017, now Pat. No. 11,826,433.

(60) Provisional application No. 62/289,961, filed on Feb. 2, 2016.

(51) Int. Cl.
| | |
|---|---|
| *A61K 48/00* | (2006.01) |
| *A61K 9/00* | (2006.01) |
| *A61K 31/351* | (2006.01) |
| *A61K 31/4706* | (2006.01) |
| *A61K 31/5415* | (2006.01) |
| *A61K 31/7016* | (2006.01) |
| *A61K 38/17* | (2006.01) |
| *A61K 47/42* | (2017.01) |
| *A61K 47/62* | (2017.01) |
| *A61K 47/64* | (2017.01) |
| *C07K 14/775* | (2006.01) |
| *C12N 15/63* | (2006.01) |
| *C12N 15/64* | (2006.01) |
| *C12N 15/79* | (2006.01) |
| *C12N 15/86* | (2006.01) |
| *C07K 5/083* | (2006.01) |

(52) U.S. Cl.
CPC ........ *A61K 48/0008* (2013.01); *A61K 9/0085* (2013.01); *A61K 31/351* (2013.01); *A61K 31/4706* (2013.01); *A61K 31/5415* (2013.01); *A61K 31/7016* (2013.01); *A61K 38/1709* (2013.01); *A61K 47/42* (2013.01); *A61K 47/62* (2017.08); *A61K 47/6455* (2017.08); *C07K 14/775* (2013.01); *C12N 15/63* (2013.01); *C12N 15/64* (2013.01); *C12N 15/79* (2013.01); *C12N 15/86* (2013.01); *C07K*

*5/0808* (2013.01); *C07K 2319/00* (2013.01); *C07K 2319/33* (2013.01); *C12N 2750/14143* (2013.01)

(58) Field of Classification Search
CPC ............ A61K 48/0008; A61K 48/0075; C07K 14/775; A61P 25/28
See application file for complete search history.

(56) References Cited

U.S. PATENT DOCUMENTS

| | | | |
|---|---|---|---|
| 5,478,745 | A | 12/1995 | Samulski et al. |
| 5,871,982 | A | 2/1999 | Wilson et al. |
| 6,156,303 | A | 12/2000 | Russell et al. |
| 6,177,403 | B1 | 1/2001 | Stedman |
| 6,251,677 | B1 | 6/2001 | Wilson et al. |
| 6,399,575 | B1 | 6/2002 | Smith et al. |
| 6,485,966 | B2 | 11/2002 | Gao et al. |
| 6,498,244 | B1 | 12/2002 | Patel et al. |
| 6,544,786 | B1 | 4/2003 | Xiao et al. |
| 6,953,690 | B1 | 10/2005 | Gao et al. |
| 6,962,815 | B2 | 11/2005 | Bartlett |
| 7,022,519 | B2 | 4/2006 | Gao et al. |
| 7,198,951 | B2 | 4/2007 | Gao et al. |
| 7,235,393 | B2 | 6/2007 | Gao et al. |
| 7,238,526 | B2 | 7/2007 | Wilson et al. |
| 7,282,199 | B2 | 10/2007 | Gao et al. |
| 7,427,396 | B2 | 9/2008 | Arbetman et al. |
| 7,456,015 | B2 | 11/2008 | Bohn et al. |
| 7,906,111 | B2 | 3/2011 | Wilson et al. |
| 8,222,221 | B2 | 7/2012 | Corey et al. |

(Continued)

FOREIGN PATENT DOCUMENTS

| | | | |
|---|---|---|---|
| EP | 2261242 | A1 | 12/2010 |
| EP | 2453923 | A2 | 5/2012 |

(Continued)

OTHER PUBLICATIONS

Extended European Search Report for Application No. EP 17748143. 9, mailed Sep. 18, 2019.

(Continued)

*Primary Examiner* — Marcia S Noble

(74) *Attorney, Agent, or Firm* — Wolf, Greenfield & Sacks, P.C.

(57) ABSTRACT

The disclosure relates, in some aspects, to compositions and methods for enhanced delivery of a transgene to the central nervous system (CNS) of a subject. In some embodiments, the transgene is delivered by recombinant AAV (rAAV). In some embodiments, the method of enhancing transgene delivery comprises administering a blood brain barrier (BBB)-crossing molecule (e.g., K16ApoE) and an rAAV comprising a transgene to a subject.

6 Claims, 10 Drawing Sheets

Specification includes a Sequence Listing.

(56) References Cited

U.S. PATENT DOCUMENTS

| | | | |
|---|---|---|---|
| 8,524,446 | B2 | 9/2013 | Gao et al. |
| 8,734,809 | B2 | 5/2014 | Gao et al. |
| 9,217,155 | B2 | 12/2015 | Gao et al. |
| 9,249,424 | B2 | 2/2016 | Wolf et al. |
| 11,826,433 | B2 | 11/2023 | Esteves et al. |
| 2001/0016355 | A1 | 8/2001 | Samulski et al. |
| 2002/0019050 | A1 | 2/2002 | Gao et al. |
| 2002/0164783 | A1 | 11/2002 | Feldhaus |
| 2002/0192823 | A1 | 12/2002 | Bartlett |
| 2003/0040101 | A1 | 2/2003 | Wilson et al. |
| 2003/0103939 | A1 | 6/2003 | Engelhardt et al. |
| 2003/0110526 | A1 | 6/2003 | Brown et al. |
| 2003/0119191 | A1 | 6/2003 | Gao et al. |
| 2003/0138772 | A1* | 7/2003 | Gao .................... C07K 14/005 |
| | | | 435/456 |
| 2003/0207259 | A1 | 11/2003 | Gao et al. |
| 2003/0228282 | A1 | 12/2003 | Gao et al. |
| 2004/0101514 | A1 | 5/2004 | Liu et al. |
| 2004/0219528 | A1 | 11/2004 | Morris et al. |
| 2005/0014262 | A1 | 1/2005 | Gao et al. |
| 2005/0032219 | A1 | 2/2005 | Aubourg et al. |
| 2005/0197313 | A1 | 9/2005 | Roelvink et al. |
| 2005/0255086 | A1 | 11/2005 | Davidson et al. |
| 2005/0255089 | A1 | 11/2005 | Chiorini et al. |
| 2005/0287122 | A1 | 12/2005 | Bartlett et al. |
| 2006/0018841 | A1 | 1/2006 | Arbetman et al. |
| 2006/0063174 | A1 | 3/2006 | Turner et al. |
| 2006/0093589 | A1 | 5/2006 | Warrington et al. |
| 2006/0153826 | A1 | 7/2006 | Arnould et al. |
| 2006/0189564 | A1 | 8/2006 | Burright et al. |
| 2006/0228800 | A1 | 10/2006 | Lin et al. |
| 2006/0292117 | A1 | 12/2006 | Loiler et al. |
| 2007/0004042 | A1 | 1/2007 | Gao et al. |
| 2007/0036760 | A1 | 2/2007 | Wilson et al. |
| 2007/0105803 | A1* | 5/2007 | Manoharan ........ A61K 31/7088 |
| | | | 514/44 A |
| 2007/0243526 | A1 | 10/2007 | Kay et al. |
| 2007/0253936 | A1 | 11/2007 | Kay et al. |
| 2007/0292410 | A1 | 12/2007 | Cashman et al. |
| 2008/0075737 | A1 | 3/2008 | Gao et al. |
| 2008/0075740 | A1 | 3/2008 | Gao et al. |
| 2008/0292595 | A1 | 11/2008 | Arbetman et al. |
| 2009/0042783 | A1 | 2/2009 | Vitek et al. |
| 2009/0042828 | A1 | 2/2009 | Xu et al. |
| 2009/0111766 | A1 | 4/2009 | Atkinson et al. |
| 2009/0149409 | A1 | 6/2009 | Bohn et al. |
| 2009/0197338 | A1 | 8/2009 | Vandenberghe et al. |
| 2009/0215879 | A1 | 8/2009 | DiPrimio et al. |
| 2009/0239240 | A1 | 9/2009 | Chu |
| 2010/0104561 | A1 | 4/2010 | Zhong et al. |
| 2010/0186103 | A1 | 7/2010 | Gao et al. |
| 2010/0323001 | A1 | 12/2010 | Pachuk |
| 2011/0171262 | A1 | 7/2011 | Bakker et al. |
| 2011/0172293 | A1 | 7/2011 | Fish et al. |
| 2011/0212520 | A1 | 9/2011 | Davidson et al. |
| 2011/0258716 | A1 | 10/2011 | Baltimore et al. |
| 2011/0306550 | A1 | 12/2011 | Vitek et al. |
| 2012/0077870 | A1 | 3/2012 | Blanks et al. |
| 2012/0137379 | A1 | 5/2012 | Gao et al. |
| 2012/0270930 | A1 | 10/2012 | Van Der Maarel et al. |
| 2012/0309050 | A1 | 12/2012 | Kumon et al. |
| 2013/0030042 | A1 | 1/2013 | Couto |
| 2013/0101558 | A1 | 4/2013 | Gao et al. |
| 2013/0109742 | A1 | 5/2013 | Hewitt et al. |
| 2013/0142861 | A1 | 6/2013 | Tsou et al. |
| 2013/0195801 | A1 | 8/2013 | Gao et al. |
| 2013/0310443 | A1 | 11/2013 | Srivastava et al. |
| 2013/0323226 | A1 | 12/2013 | Wilson et al. |
| 2014/0142161 | A1 | 5/2014 | Flotte et al. |
| 2014/0142288 | A1 | 5/2014 | Davidson et al. |
| 2014/0179770 | A1 | 6/2014 | Zhang et al. |
| 2014/0201857 | A1 | 7/2014 | Fahrenkrug et al. |
| 2014/0335054 | A1 | 11/2014 | Gao et al. |
| 2015/0065560 | A1 | 3/2015 | Bjorklund et al. |
| 2015/0258180 | A1 | 9/2015 | Mahuran et al. |
| 2016/0017005 | A1 | 1/2016 | Asokan et al. |
| 2016/0060624 | A1 | 3/2016 | Davidson et al. |
| 2016/0076054 | A1 | 3/2016 | Auricchio et al. |
| 2016/0153005 | A1 | 6/2016 | Zhang et al. |
| 2016/0185832 | A1 | 6/2016 | Drivas et al. |
| 2016/0194374 | A1 | 7/2016 | Wijnholds et al. |
| 2016/0272976 | A1 | 9/2016 | Kaspar |
| 2017/0029785 | A1 | 2/2017 | Zhao et al. |
| 2017/0114340 | A1 | 4/2017 | Mueller et al. |
| 2017/0165377 | A1 | 6/2017 | Gao et al. |
| 2019/0038773 | A1 | 2/2019 | Esteves et al. |

FOREIGN PATENT DOCUMENTS

| | | |
|---|---|---|
| EP | 2468891 A2 | 6/2012 |
| JP | 2008-538286 A | 10/2008 |
| WO | WO 2003/042397 A2 | 5/2003 |
| WO | WO 2004/108922 A2 | 12/2004 |
| WO | WO 2005/033321 A2 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/091703 A2 | 7/2008 |
| WO | WO 2008/125846 A2 | 10/2008 |
| WO | WO 2008/150897 A2 | 12/2008 |
| WO | WO 2009/043936 A1 | 4/2009 |
| WO | WO 2009/146178 A1 | 12/2009 |
| WO | WO 2010/027446 A2 | 3/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/008823 A2 | 1/2011 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 12/2014 |
| WO | WO 2015/121501 A1 | 8/2015 |
| WO | WO 2015/164786 A1 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Invitation to Pay Additional Fees for Application No. PCT/US2017/016194, mailed May 2, 2017.

International Search Report and Written Opinion for Application No. PCT/US2017/016194, mailed Jun. 27, 2017.

International Preliminary Report on Patentability for Application No. PCT/US2017/016194, mailed Aug. 16, 2018.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

Adachi et al., Drawing a high-resolution functional map of adeno-associated virus capsid by massively parallel sequencing. Nat Commun 2014;5:3075. doi: 10.1038/ncomms4075.

Afione et al., In vivo model of adeno-associated virus vector persistence and rescue. J Virol. May 1996;70(5):3235-41.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

(56) References Cited

OTHER PUBLICATIONS

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Berns et al., Detection of adeno-associated virus (AAV)-specific nucleotide sequences in DNA isolated from latently infected Detroit 6 cells. Virology. Dec. 1975;68(2):556-60.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Boillée et al., Onset and progression in inherited ALS determined by motor neurons and microglia. Science. Jun. 2, 2006;312(5778):1389-92.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alphal-antitrypsin (AAT) vector in AAT-deficient adults. Hum Gene Ther. Dec. 2006;17(12):1177-86.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., p. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.

Chen et al., Efficient transduction of vascular endothelial cells with recombinant adeno-associated virus serotype 1 and 5 vectors. Hum Gene Ther. Feb. 2005;16(2):235-47.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.

Chiorini et al., Cloning and characterization of adeno-associated virus type 5. J Virol. Feb. 1999;73(2):1309-19.

Chirmule et al., Humoral immunity to adeno-associated virus type 2 vectors following administration to murine and nonhuman primate muscle. J Virol. Mar. 2000;74(5):2420-5.

Choudhury et al., Identification of Novel vectors capable of CNS transduction in adult mice after single round selection using DNA shuffled AAV capsid library. Mol Ther. May 1, 2013;21(1):S1.

Cideciyan et al., Human RPE65 gene therapy for Leber congenital amaurosis: persistence of early visual improvements and safety at 1 year. Hum Gene Ther. Sep. 2009;20(9):999-1004.

Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.

Conlon et al., Ribozyme Approaches towards Down-Regulation of Pi*Z Mutant Human a-1 Anti-Trypsin. Mol. Therapy. 2004;9:S333. Abstract 875.

Conrad et al., Safety of single-dose administration of an adeno-associated virus (AAV)-CFTR vector in the primate lung. Gene Ther. Aug. 1996;3(8):658-68.

Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.

Cruz et al., The promise of gene therapy for the treatment of alpha-1 antitrypsin deficiency. Pharmacogenomics. Sep. 2007;8(9):1191-8.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.

Daya et al., Gene therapy using adeno-associated virus vectors. Clin Microbiol Rev. Oct. 2008;21(4):583-93. doi: 10.1128/CMR.00008-08.

Di Giorgio et al., Non-cell autonomous effect of glia on motor neurons in an embryonic stem cell-based ALS model. Nat Neurosci. May 2007;10(5):608-14. Epub Apr. 15, 2007.

Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.

Ehlert et al., Cellular toxicity following application of adeno-associated viral vector-mediated RNA interference in the nervous system. BMC Neurosci. Feb. 18, 2010;11:20.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fischer et al., Successful transgene expression with serial doses of aerosolized rAAV2 vectors in rhesus macaques. Mol Ther. Dec. 2003;8(6):918-26.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

(56) References Cited

OTHER PUBLICATIONS

Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.

Foust et al., Intravascular AAV9 preferentially targets neonatal-neurons and adult-astrocytes. Nature Biotechnology, 27; 59-65 2009.

Foust et al., Over the barrier and through the blood: to CNS delivery we go. Cell Cycle. Dec. 15, 2009;8(24):4017-8.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Fu et al., Self-complementary adeno-associated virus serotype 2 vector: global distribution and broad dispersion of AAV-mediated transgene expression in mouse brain. Mol Ther. Dec. 2003;8(6):911-7.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.

Gao et al., Adeno-associated viruses undergo substantial evolution in primates during natural infections. Proc Natl Acad Sci U S A. May 13, 2003;100(10):6081-6. Epub Apr. 25, 2003.

Gao et al., Biology of AAV serotype vectors in liver-directed gene transfer to nonhuman primates. Mol Ther. Jan. 2006;13(1):77-87. Epub Oct. 10, 2005.

Gao et al., Clades of Adeno-associated viruses are widely disseminated in human tissues. J Virol. Jun. 2004;78(12):6381-8.

Gao et al., Erythropoietin gene therapy leads to autoimmune anemia in macaques. Blood. May 1, 2004;103(9):3300-2. Epub Dec. 24, 2003.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., New recombinant serotypes of AAV vectors. Curr Gene Ther. Jun. 2005;5(3):285-97.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., RAAV-mediated targeting in adult mice and its potential in generating animal models of tissue-specific somatic transgenics or knock down. Molecular Therapy. May 2008;16(1):S118-S119. Abstract 316.

Genbank Submission; Accession No. ADZ26851; Wilson et al.; Jun. 30, 2005.

Genbank Submission; Accession No. AF028705.1; Rutledge et al.; Jan. 12, 1998.

Genbank Submission; NCBI, Accession No. AAB95450; Rutledge et al.; Jan. 12, 1998.

Genbank Submission; NCBI, Accession No. AAS99264; Gao et al.; Jun. 24, 2004.

Genbank Submission; NCBI, Accession No. ABA71701; Schmidt et al.; May 10, 2006.

Genbank Submission; NCBI, Accession No. ACB55301; Vandenberghe et al.; Jul. 31, 2008.

Genbank Submission; NCBI, Accession No. ACB55310; Vandenberghe et al.; Jul. 31, 2008.

Genbank Submission; NCBI, Accession No. AY530579.10; 2004.

Genbank Submission; NCBI, Accession No. NP_049542; Xiao et al.; Mar. 11, 2010.

Genbank Submission; NCBI, Accession No. YP_680426; Ruffing et al.; Nov. 19, 2010.

Grimm et al., Fatality in mice due to oversaturation of cellular microRNA/short hairpin RNA pathways. Nature. May 25, 2006;441(7092):537-41.

Grimm, Small silencing RNAs: state-of-the-art. Adv Drug Deliv Rev. Jul. 25, 2009;61(9):672-703. doi: 10.1016/j.addr.2009.05.002. Epub May 7, 2009.

Hadaczek et al., Widespread AAV1- and AAV2-mediated transgene expression in the nonhuman primate brain: implications for Huntington's disease. Mol Ther Methods Clin Dev. Jun. 29, 2016;3:16037. doi: 10.1038/mtm.2016.37. eCollection 2016.

Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.

Hernandez et al., Latent adeno-associated virus infection elicits humoral but not cell-mediated immune responses in a nonhuman primate model. J Virol. Oct. 1999;73(10):8549-58.

Hildinger et al., Hybrid vectors based on adeno-associated virus serotypes 2 and 5 for muscle-directed gene transfer. J Virol. Jul. 2001;75(13):6199-203.

Iida et al., Systemic Delivery of Tyrosine-Mutant AAV Vectors Results in Robust Transduction of Neurons in Adult Mice. BioMed Res Int. 2013;2013.

Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.

Jakobsson et al., Lentiviral vectors for use in the central nervous system. Mol Ther. Mar. 2006;13(3):484-93. Epub Jan. 3, 2006.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Kaspar et al., Retrograde viral delivery of IGF-1 prolongs survival in a mouse ALS model. Science. Aug. 8, 2003;301(5634):839-42.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.

Lawlor et al., Efficient gene delivery and selective transduction of glial cells in the mammalian brain by AAV serotypes isolated from nonhuman primates. Mol Ther. Oct. 2009;17(10):1692-702. doi:; 10.1038/mt.2009.170.

Lebherz et al., Gene therapy with novel adeno-associated virus vectors substantially diminishes atherosclerosis in a murine model of familial hypercholesterolemia. J Gene Med. Jun. 2004;6(6):663-72.

Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Li et al., Protein trans-splicing as a means for viral vector-mediated in vivo gene therapy. Hum Gene Ther. Sep. 2008;19(9):958-64. doi: 10.1089/hum.2008.009.

(56)     References Cited

OTHER PUBLICATIONS

Lin et al., Impact of preexisting vector immunity on the efficacy of adeno-associated virus-based HIV-1 Gag vaccines. Hum Gene Ther. Jul. 2008;19(7):663-9.

Liu et al., Biological Differences in rAAV Transduction of Airway Epithelia in Humans and in Old World Non-human Primates. Mol Ther. Dec. 2007;15(12):2114-23. Epub Jul. 31, 2007.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Loiler et al., Targeting recombinant adeno-associated virus vectors to enhance gene transfer to pancreatic islets and liver. Gene Ther. Sep. 2003;10(18):1551-8.

Lowenstein, Crossing the rubicon. Nat Biotechnol. Jan. 2009;27(1):42-4.

Lux et al., Green fluorescent protein-tagged adeno-associated virus particles allow the study of cytosolic and nuclear trafficking. J Virol. Sep. 2005;79(18):11776-87.

Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.

Maguire et al., Gene therapy for the nervous system: challenges and new strategies. Neurotherapeutics. Oct. 2014;11(4):817-39. doi: 10.1007/s13311-014-0299-5.

Mandel et al., Recombinant adeno-associated viral vectors as therapeutic agents to treat neurological disorders. Mol Ther. Mar. 2006;13(3):463-83. Epub Jan. 18, 2006.

Manfredsson et al., AAV9: a potential blood-brain barrier buster. Mol Ther. Mar. 2009;17(3):403-5.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Matalon et al., Adeno-associated virus-mediated aspartoacylase gene transfer to the brain of knockout mouse for canavan disease. Mol Ther. May 2003;7(5 Pt 1):580-7.

Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.

Mcbride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

Mccarty et al., Adeno-associated virus terminal repeat (TR) mutant generates self-complementary vectors to overcome the rate-limiting step to transduction in vivo. Gene Ther. Dec. 2003;10(26):2112-8.

Mccarty et al., Integration of adeno-associated virus (AAV) and recombinant AAV vectors. Annu Rev Genet. 2004;38:819-45.

Mccarty et al., Self-complementary recombinant adeno-associated virus (scAAV) vectors promote efficient transduction independently of DNA synthesis. Gene Ther. Aug. 2001;8(16):1248-54.

Mccarty, Self-complementary AAV vectors; advances and applications. Mol Ther. Oct. 2008; 16(10):1648-56. Epub Aug. 5, 2008.

Mccurdy et al., Sustained normalization of neurological disease after intracranial gene therapy in a feline model. Sci Transl Med. Apr. 9, 2014;6(231):231ra48. doi: 10.1126/scitranslmed.3007733.

Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.

Mingozzi et al., CD8(+) T-cell responses to adeno-associated virus capsid in humans. Nat Med. Apr. 2007;13(4):419-22. Epub Mar. 18, 2007.

Moffett et al., N-Acetylaspartate in the CNS: from neurodiagnostics to neurobiology. Prog Neurobiol. Feb. 2007;81(2):89-131. Epub Jan. 5, 2007.

Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004; 125(2):509-21.

Mousazadeh et al., Gene delivery to brain cells with apoprotein E derived peptide conjugated to polylysine (apoEdp-PLL). J Drug Target. Apr. 2007;15(3):226-30. doi: 10.1080/10611860601148908.

Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

Mueller et al., In Vivo AAV Delivered Allele Specific shRNA for the Knockdown of Alpha-1 Antitrypsin. Molecular Therapy May 2010;18(1):S22. Abstract 53.

Mueller et al., In Vivo Allele Specific Knockdown of Mutant Alpha-1 Antitrypsin Using Recombinant AAV Delivered shRNA. Molecular Therapy May 2009;17(1):S313. Abstract 817.

Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.

Mueller et al., The pros and cons of immunomodulatory IL-10 gene therapy with recombinant AAV in a Cftr-/--dependent allergy mouse model. Gene Ther. Feb. 2009;16(2):172-83. Epub Sep. 25, 2008.

Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.

NCBI Blast Protein Sequence. RID-09JSKF33114. Alignment of Seq ID Nos. 87, 179. 2016.

Nonnenmacher et al., Intracellular transport of recombinant adeno-associated virus vectors. Gene Ther. Jun. 2012; 19(6):649-58. doi: 10.1038/gt.2012.6. Epub Feb. 23, 2012.

O'Reilly et al., RNA interference-mediated suppression and replacement of human rhodopsin in vivo. Am J Hum Genet. Jul. 2007;81(1):127-35. Epub May 23, 2007.

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.

Ralph et al., Silencing mutant SOD1 using RNAi protects against neurodegeneration and extends survival in an ALS model. Nat Med. Apr. 2005;11(4):429-33. Epub Mar. 13, 2005.

Raoul et al., Lentiviral-mediated silencing of SOD1 through RNA interference retards disease onset and progression in a mouse model of ALS. Nat Med. Apr. 2005;11(4):423-8. Epub Mar. 13, 2005.

Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.

Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.

Schnepp et al., Characterization of adeno-associated virus genomes isolated from human tissues. J Virol. Dec. 2005;79(23):14793-803.

Seiler et al., Adeno-associated virus types 5 and 6 use distinct receptors for cell entry. Hum Gene Ther. Jan. 2006;17(1):10-9.

Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.

Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.

(56) References Cited

OTHER PUBLICATIONS

Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.

Stoica et al., Targeting Human SOD1 Using AAV mediated RNAi in a mouse model of amyotrophic lateral sclerosis. Mol ther. Jun. 2013;21(1):S149.

Storek et al., Intrathecal long-term gene expression by self-complementary adeno-associated virus type 1 suitable for chronic pain studies in rats. Mol Pain. Jan. 30, 2006;2:4.

Storkebaum et al., Treatment of motoneuron degeneration by intracerebroventricular delivery of VEGF in a rat model of ALS. Nat Neurosci. Jan. 2005;8(1):85-92. Epub Nov. 28, 2004.

Suckau et al., 851. The Effect of Genome Size and Design of scAAV Vectors on Efficiency of shRNA Expression and Gene Knockdown. May 1, 2007;15(1):S325.

Tenenbaum et al., Recombinant AAV-mediated gene delivery to the central nervous system. J Gene Med. Feb. 2004;6 Suppl 1:S212-22.

Tomar et al., Use of adeno-associated viral vector for delivery of small interfering RNA. Oncogene. Aug. 28, 2003;22(36):5712-5.

Towne et al., Systemic AAV6 delivery mediating RNA interference against SOD1: neuromuscular transduction does not alter disease progression in fALS mice. Mol Ther. Jun. 2008;16(6):1018-25. doi: 10.1038/mt.2008.73. Epub Apr. 15, 2008.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.

Uniprot Submission; Accession No. A8IGP7; Nov. 13, 2013.

Uniprot Submission; Accession No. H3GK32; Feb. 6, 2013.

Uniprot Submission; Accession No. T2BRA8; Nov. 13, 2013.

Vandenberghe et al., Heparin binding directs activation of T cells against adeno-associated virus serotype 2 capsid. Nat Med. Aug. 2006;12(8):967-71. Epub Jul. 16, 2006.

Vandenberghe et al., Tailoring the AAV vector capsid for gene therapy. Gene Ther. Mar. 2009;16(3):311-9. Epub Dec. 4, 2008.

Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.

Virella-Lowell et al., Enhancing rAAV vector expression in the lung. J Gene Med. Jul. 2005;7(7):842-50.

Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.

Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.

Wang et al., Somatically Repairing Compound Heterozygous Recessive Mutations by Chromosomal Cut-and-Paste for in Vivo Gene Therapy. May 2016. 24(1):S289. Abstract 733.

Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.

Wang et al., The design of vectors for RNAi delivery system. Curr Pharm Des. 2008;14(13):1327-40.

Wang et al., The next step in gene delivery: molecular engineering of adeno-associated virus serotypes. J Mol Cell Cardiol. May 2011;50(5):793-802. doi: 10.1016/j.yjmcc.2010.10.017. Epub Oct. 26, 2010.

Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.

Wein et al., Efficient bypass of mutations in dysferlin deficient patient cells by antisense-induced exon skipping. Hum Mutat. Feb. 2010;31(2):136-42. doi: 10.1002/humu.21160.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.

Wu et al., Alpha2,3 and alpha2,6 N-linked sialic acids facilitate efficient binding and transduction by adeno-associated virus types 1 and 6. J Virol. Sep. 2006;80(18):9093-103.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1):S262. Abstract 671.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 2, 2010.

Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1):S140. Abstract362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

Yan et al., Unique biologic properties of recombinant AAV1 transduction in polarized human airway epithelia. J Biol Chem. Oct. 6, 2006;281(40):29684-92. Epub Aug. 9, 2006.

Zabner et al., Adeno-associated virus type 5 (AAV5) but not AAV2 binds to the apical surfaces of airway epithelia and facilitates gene transfer. J Virol. Apr. 2000;74(8):3852-8.

Zhang et al., Characterization of 12 AAV vectors for intravascular delivery to target CNS and detarget non-CNS tissues by mirna

(56) References Cited

OTHER PUBLICATIONS regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Zou et al., Cell-penetrating Peptide-mediated therapeutic molecule delivery into the central nervous system. Curr Neuropharmacol. Mar. 2013;11(2):197-208. doi: 10.2174/1570159X11311020006.

* cited by examiner

AAV9

AAV9
+ K16ApoE forebrain midbrain

AAV9

AAV9 + K16ApoE cerebellum and brainstem spinal cord

AAV9

AAV9 + k16aPOe motor cortex somatosensory cortex striatum

SEQUENCE LISTING

Sequence total quantity: 23
SEQ ID NO: 1          moltype = AA  length = 736
FEATURE               Location/Qualifiers
REGION                1..736
                      note = Synthetic Polypeptide
source                1..736
                      mol_type = protein
                      organism = synthetic construct
SEQUENCE: 1
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPPPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                   736

SEQ ID NO: 2          moltype = AA  length = 735
FEATURE               Location/Qualifiers
REGION                1..735
                      note = Synthetic Polypeptide
source                1..735
                      mol_type = protein
                      organism = synthetic construct
SEQUENCE: 2
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IPFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRF LTRNL                                                    735

SEQ ID NO: 3          moltype = AA  length = 735
FEATURE               Location/Qualifiers
REGION                1..735
                      note = Synthetic Polypeptide
source                1..735

```
                         mol_type = protein
                         organism = synthetic construct
SEQUENCE: 3
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQQQNTAP ATADVNTQGV   600
LPGMVWQDRD VYLQGPIWAK IPHTDGHFHP SPLMGGFGLK HPPPQILIKN TPVPANPSTT   660
FSAAKFASFI TQYSTGQVSV EIEWELQKEN SKRWNPEIQY TSNYNKSVNV DFTVDTNGVY   720
SEPRPIGTRF LTRNL                                                   735

SEQ ID NO: 4           moltype = AA  length = 736
FEATURE                Location/Qualifiers
REGION                 1..736
                       note = Synthetic Polypeptide
source                 1..736
                       mol_type = protein
                       organism = synthetic construct
SEQUENCE: 4
MAADGYLPDW LEDTLSEGIR QWWKLKPGPP PPKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTQNDGT TTIANNLTST VQVFTDSEYQ LPYVLGSAHQ   360
GCLPPFPADV FMVPQYGYLT LNNGSQAVGR SSFYCLEYFP SQMLRTGNNF TFSYTFEDVP   420
FHSSYAHSQS LDRLMNPLID QYLYYLSRTN TPSGTTTQSR LQFSQAGASD IRDQSRNWLP   480
GPCYRQQRVS KTSADNNNSE YSWTGATKYH LNGRDSLVNP GPAMASHKDD EEKFFPQSGV   540
LIFGKQGSEK TNVDIEKVMI TDEEEIRTTN PVATEQYGSV STNLQRGNRQ AATADVNTQG   600
VLPGMVWQDR DVYLQGPIWA KIPHTDGHFH PSPLMGGFGL KHPPPQILIK NTPVPANPST   660
TFSAAKFASF ITQYSTGQVS VEIEWELQKE NSKRWNPEIQ YTSNYAKSAN VDFTVDNNGV   720
YSEPRPIGTR FLTRNL                                                  736

SEQ ID NO: 5           moltype = AA  length = 736
FEATURE                Location/Qualifiers
REGION                 1..736
                       note = Synthetic Polypeptide
source                 1..736
                       mol_type = protein
                       organism = synthetic construct
SEQUENCE: 5
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPFG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD KDKFFPMSGV   540
MIFGKESAGA SNTALDNVMI TDEEEIKATN PVATERFGTV AVNLQSSSTD PATGDVHVMG   600
ALPGMVWQDR DVYLQGPIWA KIPHTDGHFH PSPLMGGFGL KHPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                  736

SEQ ID NO: 6           moltype = AA  length = 738
FEATURE                Location/Qualifiers
REGION                 1..738
                       note = Synthetic Polypeptide
source                 1..738
                       mol_type = protein
                       organism = synthetic construct
SEQUENCE: 6
MAADGYLPDW LEDNLSEGIR EWWALKPGAP KPKANQQKQD DGRGLVLPGY KYLGPFNGLD    60
KGEPVNAADA AALEHDKAYD QQLQAGDNPY LRYNHADAEF QERLQEDTSF GGNLGRAVFQ   120
AKKRVLEPLG LVEEGAKTAP GKKRPVEPSP QRSPDSSTGI GKKGQQPARK RLNFGQTGDS   180
ESVPDPQPLG EPPAAPSGVG PNTMAAGGGA PMADNNEGAD GVGSSSGNWH CDSTWLGDRV   240
ITTSTRTWAL PTYNNHLYKQ ISNGTSGGAT NDNTYFGYST PWGYFDFNRF HCHFSPRDWQ   300
RLINNNWGFR PKRLSFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NPQFTYTFED   420
VPFHSSYAHS QSLDRLMNPL IDQYLYYLSR TQTTGGTANT QTLGFSQGGP NTMANQAKNW   480
LPGPCYRQQR VSTTTGQNNN SNFAWTAGTK YHLNGRNSLA NPGIAMATHK DDEERFFPSN   540
GILIFGKQNA ARDNADYSDV MLTSEEEIKT TNPVATEEYG IVADNLQQQN TAPQIGTVNS   600
```

```
QGALPGMVWQ NRDVYLQGPI WAKIPHTDGN FHPSPLMGGF GLKHPPPQIL IKNTPVPADP   660
PTTFNQSKLN SFITQYSTGQ VSVEIEWELQ KENSKRWNPE IQYTSNYYKS TSVDFAVNTE   720
GVYSEPRPIG TRYLTRNL                                                 738

SEQ ID NO: 7               moltype = AA   length = 736
FEATURE                    Location/Qualifiers
REGION                     1..736
                           note = Synthetic Polypeptide
source                     1..736
                           mol_type = protein
                           organism = synthetic construct
SEQUENCE: 7
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KTGQQPAKKR LNFGQTGDSE   180
SVPDPQPLGE PPAAPSGLGP NTMASGGGAP MADNNEGADG VGNSSGNWHC DSTWLGDRVI   240
TTSTRTWALP TYNNHLYKQI SNGTSGGSTN DNTYFGYSTP WGYFDFNRFH CHFSPRDWQR   300
LINNNWGFRP KRLNFKLFNI QVKEVTTNEG TKTIANNLTS TVQVFTDSEY QLPYVLGSAH   360
QGCLPPFPAD VFMVPQYGYL TLNNGSQALG RSSFYCLEYF PSQMLRTGNN FQFSYTFEDV   420
PFHSSYAHSQ SLDRLMNPLI DQYLYYLVRT QTTGTGGTQT LAFSQAGPSS MANQARNWVP   480
GPCYRQQRVS TTTNQNNNSN FAWTGAAKFK LNGRDSLMNP GVAMASHKDD DDRFFPSSGV   540
LIFGKQGAGN DGVDYSQVLI TDEEEIKATN PVATEEYGAV AINNQAANTQ AQTGLVHNQG   600
VIPGMVWQNR DVYLQGPIWA KIPHTDGNFH PSPLMGGFGL KHPPPQILIK NTPVPADPPL   660
TFNQAKLNSF ITQYSTGQVS VEIEWELQKE NSKRWNPEIQ YTSNYYKSTN VDFAVNTEGV   720
YSEPRPIGTR YLTRNL                                                   736

SEQ ID NO: 8               moltype = AA   length = 736
FEATURE                    Location/Qualifiers
REGION                     1..736
                           note = Synthetic Polypeptide
source                     1..736
                           mol_type = protein
                           organism = synthetic construct
SEQUENCE: 8
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAQ AQTGWVQNQG   600
ILPGMVWQDR DVYLQGPIWA KIPHTDGNFH PSPLMGGFGM KHPPPQILIK NTPVPADPPT   660
AFNKDKLNSF ITQYSTGQVS VEIEWELQKE NSKRWNPEIQ YTSNYYKSNN VEFAVNTEGV   720
YSEPRPIGTR YLTRNL                                                   736

SEQ ID NO: 9               moltype = AA   length = 738
FEATURE                    Location/Qualifiers
REGION                     1..738
                           note = Synthetic Polypeptide
source                     1..738
                           mol_type = protein
                           organism = synthetic construct
SEQUENCE: 9
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ   120
AKKRVLEPLG LVEEGAKTAP GKKRPVEPSP QRSPDSSTGI GKKGQQPAKK RLNFGQTGDS   180
ESVPDPQPIG EPPAGPSGLG SGTMAAGGGA PMADNNEGAD GVGNSSGNWH CDSTWLGDRV   240
ITTSTRTWAL PTYNNHLYKQ ISNGTSGGST NDNTYFGYST PWGYFDFNRF HCHFSPRDWQ   300
RLINNNWGFR PKRLNFKLFN IQVKEVTQNE GTKTIANNLT STIQVFTDSE YQLPYVLGSA   360
HQGCLPPFPA DVFMIPQYGY LTLNNGSQAV GRSSFYCLEY FPSQMLRTGN NFEFSYQFED   420
VPFHSSYAHS QSLDRLMNPL IDQYLYYLSR TQSTGGTAGT QQLLFSQAGP NNMSAQAKNW   480
LPGPCYRQQR VSTTLSQNNN SNFAWTGATK YHLNGRDSLV NPGVAMATHK DDEERFFPSS   540
GVLMFGKQGA GKDNVDYSSV MLTSEEEIKT TNPVATEQYG VVADNLQQQN AAPIVGAVNS   600
QGALPGMVWQ NRDVYLQGPI WAKIPHTDGN FHPSPLMGGF GLKHPPPQIL IKNTPVPADP   660
PTTFSQAKLA SFITQYSTGQ VSVEIEWELQ KENSKRWNPE IQYTSNYYKS TNVDFAVNTD   720
GTYSEPRPIG TRYLTRNL                                                 738

SEQ ID NO: 10              moltype = AA   length = 737
FEATURE                    Location/Qualifiers
REGION                     1..737
                           note = Synthetic Polypeptide
source                     1..737
                           mol_type = protein
                           organism = synthetic construct
SEQUENCE: 10
MAADGYLPDW LEDNLSEGIR EWWDLKPGAP KPKANQQKQD DGRGLVLPGY KYLGPFNGLD   60
```

-continued

```
KGEPVNAADA AALEHDKAYD QQLKAGDNPY LRYNHADVEF QERLQEDTSF GGNLGRAVFQ   120
AKKRVLEPFG LVEEGAKTAP GKKRPVEQSP QEPDSSSGIG KKGQQPARKR LNFGQTGDSE   180
SVPDPQPLGE PPAAPSGVGP NTMAAGGGAP MADNNEGADG VGNSSGNWHC DSTWMGDRVI   240
TTSTRTWALP TYNNHLYKQI SNGTSGGSTN DNTYFGYSTP WGYFDFNRFH CHFSPRDWQR   300
LINNNWGFRP KRLSFKLFNI QVKEVTQNEG TKTIANNLTS TIQVFTDSEY QLPYVLGSAH   360
QGCLPPFPAD VFMIPQYGYL TLNNGSQAVG RSSFYCLEYF PSQMLRTGNN FEFSYQFEDV   420
PPHSSYAHSQ SLDRLMNPLI DQYLYYLSRT QSTGGTARTQ QLLFSQAGPN TMANQAKNWL   480
PGPCYRQQRV STTTGQNNNS NSAWTAGTKY HLNGRNSLAN PGIAMATHKD DEERFFPSNG   540
ILIFGKQNAA RDNADYSDVM LTSEEEIKTT NPVATEEYGI VADNLQQQNT APQIGTVNSQ   600
GALPGMVWQN RDVYLQGPIW AKIPHTDGNF HPSPLMGGFG LKHPPPQILI KNTPVPADPP   660
TTFNQSKLNS FITQYSTGQV SVEIEWELQK ENSKRWNPEI QYTSNYYKST SVDFAVNTEG   720
VYSEPRPIGT RYLTRNL                                                 737

SEQ ID NO: 11         moltype = AA  length = 623
FEATURE               Location/Qualifiers
REGION                1..623
                      note = Synthetic Polypeptide
source                1..623
                      mol_type = protein
                      organism = synthetic construct
SEQUENCE: 11
MAAAAAAAAA AAAAAAAAAA GGGGSAPGKK RPVEQSPQEP DSSAGIGKSG AQPAKKRLNF    60
GQTGDTESVP DPQPIGEPPA APSGVGSLTM ASGGGAPVAD NNEGADGVGS SSGNWHCDSQ   120
WLGDRVITTS TRTWALPTYN NHLYKQISNS TSGGSSNDNA YFGYSTPWGY FDFNRFHCHF   180
SPRDWQRLIN NNWGFRPKRL NFKLFNIQVK EVTDNNGVKT IANNLTSTVQ VFTDSDYQLP   240
YVLGSAHEGC LPPFPADVFM IPQYGYLTLN DGSQAVGRSS FYCLEYFPSQ MLRTGNNFQF   300
SYEFENVPFH SSYAHSQSLD RLMNPLIDQY LYYLSKTING SGQNQQTLKF SVAGPSNMAV   360
QGRNYIPGPS YRQQRVSTTV TQNNYSEFAW PGASSWALNG RNSLMNPGPA MASHKEGEDR   420
FFPLSGSLIF GKQGTGRDNV DADKVMITNE EEIKTTNPVA TESYGQVATN HQSAQAQAQT   480
GWVQNQGIFP GMVWQDRDVY LQGPIWAKIP HTDGNFHPSP LMGGFGMKHP PPQILIKNTP   540
VPADPPTAFN KDKLNSFITQ YSTGQVSVEI EWELQKENSK RWNPEIQYTS NYYKSNNVEF   600
AVNTEGVYSE PRPIGTRYLT RNL                                          623

SEQ ID NO: 12         moltype = AA  length = 623
FEATURE               Location/Qualifiers
REGION                1..623
                      note = Synthetic Polypeptide
source                1..623
                      mol_type = protein
                      organism = synthetic construct
SEQUENCE: 12
MTFFYGGSRG KRNNFKTEEY GGGGSAPGKK RPVEQSPQEP DSSAGIGKSG AQPAKKRLNF    60
GQTGDTESVP DPQPIGEPPA APSGVGSLTM ASGGGAPVAD NNEGADGVGS SSGNWHCDSQ   120
WLGDRVITTS TRTWALPTYN NHLYKQISNS TSGGSSNDNA YFGYSTPWGY FDFNRFHCHF   180
SPRDWQRLIN NNWGFRPKRL NFKLFNIQVK EVTDNNGVKT IANNLTSTVQ VFTDSDYQLP   240
YVLGSAHEGC LPPFPADVFM IPQYGYLTLN DGSQAVGRSS FYCLEYFPSQ MLRTGNNFQF   300
SYEFENVPFH SSYAHSQSLD RLMNPLIDQY LYYLSKTING SGQNQQTLKF SVAGPSNMAV   360
QGRNYIPGPS YRQQRVSTTV TQNNYSEFAW PGASSWALNG RNSLMNPGPA MASHKEGEDR   420
FFPLSGSLIF GKQGTGRDNV DADKVMITNE EEIKTTNPVA TESYGQVATN HQSAQAQAQT   480
GWVQNQGIFP GMVWQDRDVY LQGPIWAKIP HTDGNFHPSP LMGGFGMKHP PPQILIKNTP   540
VPADPPTAFN KDKLNSFITQ YSTGQVSVEI EWELQKENSK RWNPEIQYTS NYYKSNNVEF   600
AVNTEGVYSE PRPIGTRYLT RNL                                          623

SEQ ID NO: 13         moltype = AA  length = 623
FEATURE               Location/Qualifiers
REGION                1..623
                      note = Synthetic Polypeptide
source                1..623
                      mol_type = protein
                      organism = synthetic construct
SEQUENCE: 13
MTFFYGGSRG KRNNFKTEEY GGGGSAPGKK RPVEQSPQEP DSSAGIGKSG AQPAKKRLNF    60
GQTGDTESVP DPQPIGEPPA APSGVGSLTM ASGGGAPVAD NNEGADGVGS SSGNWHCDSQ   120
WLGDRVITTS TRTWALPTYN NHLYKQISNS TSGGSSNDNA YFGYSTPWGY FDFNRFHCHF   180
SPRDWQRLIN NNWGFRPKRL NFKLFNIQVK EVTDNNGVKT IANNLTSTVQ VFTDSDYQLP   240
YVLGSAHEGC LPPFPADVFM IPQYGYLTLN DGSQAVGRSS FYCLEYFPSQ MLRTGNNFQF   300
NYEFENVPFH SSYAHSQSLD RLMNPLIDQY LYYLSKTIND SGQNQQTLKF SVAGPSNMAV   360
QGRNYIPGPS YRQQRVSTTV TQNNSEFAW  PGASSWALNG RNSLMNPGPA MASHKEGEDR   420
FFPLSGSLIF GKQGTGRDNV DADEVMITNE EEIKTTNPVA TESYGQVAIN HQSAQAQAQT   480
GWVQNQGILP GMVWQDRDVY LQGPIWAKIP HTDGNFHPSP LMGGFGMKHP PPQILIKNTP   540
VPADPPTAFN KDKLNSFITQ YSTGQVSVEI EWELQKENSK RWNPEIQYTS NYYKSNNVEF   600
AVNTEGVYSE PRPIGTRYLT RNL                                          623

SEQ ID NO: 14         moltype = AA  length = 623
FEATURE               Location/Qualifiers
REGION                1..623
                      note = Synthetic Polypeptide
source                1..623
                      mol_type = protein
```

-continued

```
                                organism = synthetic construct
SEQUENCE: 14
MAAAAAAAAA AAAAAAAAAA GGGGSAPGKK RPVEQSPQEP DSSAGIGKSG AQPAKKRLNF    60
GQTGDTESVP DPQPIGEPPA APSGVGSLTM ASGGGAPVAD NNEGADGVGS SSGNWHCDSQ   120
WLGDRVITTS TRTWALPTYN NHLYKQISNS TSGGSSNDNA YFGYSTPWGY FDFNRFHCHF   180
SPRDWQRLIN NNWGFRPKRL NFKLFNIQVK EVTDNNGVKT IANNLTSTVQ VFTDSDYQLP   240
YVLGSAHEGC LPPFPADVFM IPQYGYLTLN DGSQAVGRSS FYCLEYFPSQ MLRTGNNFQF   300
NYEFENVPFH SSYAHSQSLD RLMNPLIDQY LYYLSKTIND SGQNQQTLKF SVAGPSNMAV   360
QGRNYIPGPS YRQQRVSTTV TQNNNSEFAW PGASSWALNG RNSLMNPGPA MASHKEGEDR   420
FFPLSGSLIF GKQGTGRDNV DADEVMITNE EEIKTTNPVA TESYGQVAIN HQSAQAQAQT   480
GWVQNQGILP GMVWQDRDVY LQGPIWAKIP HTDGNFHPSP LMGGFGMKHP PPQILIKNTP   540
VPADPPTAFN KDKLNSFITQ YSTGQVSVEI EWELQKENSK RWNPEIQYTS NYYKSNNVEF   600
AVNTEGVYSE PRPIGTRYLT RNL                                          623

SEQ ID NO: 15              moltype = AA  length = 19
FEATURE                    Location/Qualifiers
REGION                     1..19
                           note = Synthetic Polypeptide
source                     1..19
                           mol_type = protein
                           organism = synthetic construct
SEQUENCE: 15
TFFYGGSRGK RNNFKTEEY                                                19

SEQ ID NO: 16              moltype = AA  length = 19
FEATURE                    Location/Qualifiers
REGION                     1..19
                           note = Synthetic Polypeptide
source                     1..19
                           mol_type = protein
                           organism = synthetic construct
SEQUENCE: 16
AAAAAAAAAA AAAAAAAAA                                                19

SEQ ID NO: 17              moltype = AA  length = 36
FEATURE                    Location/Qualifiers
REGION                     1..36
                           note = Synthetic Polypeptide
source                     1..36
                           mol_type = protein
                           organism = synthetic construct
SEQUENCE: 17
KKKKKKKKKK KKKKKKLRVR LASHLRKLRK RLLRDA                             36

SEQ ID NO: 18              moltype = AA  length = 4
FEATURE                    Location/Qualifiers
REGION                     1..4
                           note = Synthetic Polypeptide
source                     1..4
                           mol_type = protein
                           organism = synthetic construct
SEQUENCE: 18
KKKK                                                                4

SEQ ID NO: 19              moltype = AA  length = 8
FEATURE                    Location/Qualifiers
REGION                     1..8
                           note = Synthetic Polypeptide
source                     1..8
                           mol_type = protein
                           organism = synthetic construct
SEQUENCE: 19
KKKKKKKK                                                            8

SEQ ID NO: 20              moltype = AA  length = 12
FEATURE                    Location/Qualifiers
REGION                     1..12
                           note = Synthetic Polypeptide
source                     1..12
                           mol_type = protein
                           organism = synthetic construct
SEQUENCE: 20
KKKKKKKKKK KK                                                       12

SEQ ID NO: 21              moltype = AA  length = 16
FEATURE                    Location/Qualifiers
REGION                     1..16
                           note = Synthetic Polypeptide
source                     1..16
```

-continued

```
                        mol_type = protein
                        organism = synthetic construct
SEQUENCE: 21
KKKKKKKKKK KKKKK                                              16

SEQ ID NO: 22           moltype = AA  length = 20
FEATURE                 Location/Qualifiers
REGION                  1..20
                        note = Synthetic Polypeptide
source                  1..20
                        mol_type = protein
                        organism = synthetic construct
SEQUENCE: 22
KKKKKKKKKK KKKKKKKKKK                                         20

SEQ ID NO: 23           moltype = AA  length = 20
FEATURE                 Location/Qualifiers
REGION                  1..20
                        note = Synthetic Polypeptide
source                  1..20
                        mol_type = protein
                        organism = synthetic construct
SEQUENCE: 23
LRVRLASHLR KLRKRLLRDA                                         20
```

METHOD TO ENHANCE THE EFFICIENCY OF SYSTEMIC AAV GENE DELIVERY TO THE CENTRAL NERVOUS SYSTEM

RELATED APPLICATIONS

This application is a continuation under U.S.C. § 120 of U.S. Application Ser. No. 16/074,968, filed Aug. 2, 2018, which is a National Stage Application of PCT/US2017/016194, filed Feb. 2, 2017, entitled "METHOD TO ENHANCE THE EFFICIENCY OF SYSTEMIC AAV GENE DELIVERY TO THE CENTRAL NERVOUS SYSTEM" which claims the benefit under 35 U.S.C. § 119 (e) of U.S. provisional Application No. 62/289,961, filed Feb. 2, 2016, entitled "METHOD TO ENHANCE THE EFFICIENCY OF SYSTEMIC AAV GENE DELIVERY TO THE CENTRAL NERVOUS SYSTEM", the entire contents of each application which are incorporated herein by reference.

REFERENCE TO AN ELECTRONIC SEQUENCE LISTING

The contents of the electronic sequence listing (U012070076US02-SEQ-LJG.xml; Size: 39,539 bytes; and Date of Creation: Oct. 18, 2023) is herein incorporated by reference in its entirety.

BACKGROUND

The discovery that certain viral vectors (e.g., AAV vectors, such as AAV9) cross the blood brain barrier (BBB) after intravascular infusion and transduce cells in the CNS started a revolution in the field of gene therapy for neurological diseases. However, the efficiency of viral vector-mediated neuronal transduction is generally very low in most CNS regions, both in the neonatal period and in adult animals, where transgene expression is limited mostly to astrocytes and endothelial cells. Attempts have been made to enhance AAV-mediated CNS gene transfer after systemic administration, for example through the development of more potent capsids, and the combination of rAAV with agents known to disrupt the BBB, such as mannitol. Generally, the combination of AAV with BBB disrupting drugs has shown only modest to no effect on the efficiency of CNS gene transfer. New approaches are needed to achieve high efficiency gene transfer to the CNS.

SUMMARY

Aspects of the disclosure relate to compositions and methods for increased efficiency of gene transfer to the CNS. In some embodiments, the disclosure is based, in part, on the surprising discovery that viral vector-mediated delivery of nucleic acids to the CNS of a subject can be enhanced by administering the viral vector with a composition comprising a highly hydrophilic molecule conjugated to a blood brain barrier (BBB)-receptor ligand (e.g., K16ApoE).

Accordingly, in some aspects the disclosure provides a method for delivering a transgene to CNS tissue in a subject, the method comprising administering to the subject; (i) an effective amount of a targeting composition, wherein the targeting composition comprises a hydrophilic peptide between 4 and 50 amino acids in length linked to a blood brain barrier (BBB) receptor targeting agent; and, an effective amount of a nucleic acid comprising a promoter operably linked to a transgene.

In some aspects, the disclosure provides a method for treating central nervous system (CNS) disease in a subject, the method comprising administering to the subject ((i) an effective amount of a targeting composition, wherein the targeting composition comprises a hydrophilic peptide between 4 and 50 amino acids in length linked to a blood brain barrier (BBB) receptor targeting agent; and, an effective amount of a nucleic acid comprising a promoter operably linked to a CNS-associated transgene.

In some embodiments, the CNS disease is selected from the group consisting of; Huntington's disease (HD), amyotrophic lateral sclerosis (ALS), and lysosomal storage disorder (LSD). In some embodiments, the lysosomal storage disorder is selected from the group consisting of: GM1 gangliosidosis, Tay-Sachs disease, and Sandhoff disease.

In some embodiments, the nucleic acid is delivered via a retrovirus vector, an adenovirus vector, a Herpes simplex virus (HSV) vector, or an adeno-associated virus (AAV) vector.

In some aspects, the disclosure provides a composition comprising (i) a nucleic acid encoding a transgene; and, (ii) a targeting composition, wherein the targeting composition comprises a hydrophilic peptide between 4 and 50 amino acids in length linked to a blood brain barrier (BBB) receptor targeting agent. In some embodiments, compositions described herein are contained within a host cell (e.g., a bacterial cell, an insect cell, or a eukaryotic cell, such as a mammalian cell). In some embodiments, the composition further comprises an effective amount of an inhibitor of endocytosis (e.g., chloroquine). In some embodiments, the composition further comprises a pharmaceutically acceptable excipient.

In some embodiments, the nucleic acid is contained in a retrovirus vector, an adenovirus vector, a Herpes simplex virus (HSV) vector, or an adeno-associated virus (AAV) vector.

In some embodiments, the viral vector is a recombinant AAV (rAAV) comprising (i) at least one inverted terminal repeat; (ii) at least one capsid protein; and, (iii) a nucleic acid comprising a promoter operably linked to a transgene.

In some embodiments, the at least one capsid protein of a viral vector described herein can be of AAV serotype. In some embodiments, the at least one capsid protein has a serotype selected from the group consisting of AAV1, AAV2. AAV2i8. AAV2.5. AAV6. AAV8, AAVrh8, AAV9, AAVrh10, AAV-B1, AAV9.45A-String (e.g., AAV9.45-AS), AAV9.45Angiopep, AAV9.47-Angiopep, and AAV9.47-AS.

In some embodiments, the at least one capsid protein comprises or consists of a sequence selected from the group consisting of SEQ ID NO: 1-14.

In some embodiments, the at least one capsid protein comprises an N-terminally grafted heterologous targeting peptide. In some embodiments, the N-terminally grafted heterologous targeting peptide comprises or consists of a sequence selected from the group consisting of SEQ ID NO: 15-16. In some embodiments, the at least one capsid protein comprises or consists of a sequence selected from the group consisting of SEQ ID NO: 10-14. In some embodiments, the N-terminally grafted heterologous targeting peptide is expressed on the surface of the rAAV.

In some embodiments, the at least one capsid protein is a VP2 capsid protein. In some embodiments, the rAAV comprises two capsid proteins, wherein each of the two capsid proteins has a different amino acid sequence (e.g., each capsid having a different serotype, or a wild type capsid and a mutant capsid having the same serotype).

In some embodiments, the transgene is a CNS-associated transgene and is selected from the group consisting of ALS2, ANG, ATXN2, C9orf72, DCTN1, FIG4, FUS, NEFH, OPTN, PFN1, PRPH, SETX, SIGMAR1, SMN1, SOD1, SPG11, TARDBP, UBQLN2, VAPB, VCP, Htt, Xbp1s, CRAG, MAN2B1, MAN2B2, MAN2C1, AGA, CLN1, CLN2, CLN3, CLN5, CLN6, MFSD8, CLN8, CTSD, MANBA, CTNS, LAMP2, GLA, ASAH1, FUCA1, CTSA, GBA, GALC, GLB1, HEXA, HEXB, ARSA, IDUA, IDS, SGSH, NAGLU, HGSNAT, GNS, GALNS, ARSB, GUSB, HYAL1, SMPD1, NPC1, NPC2, GAA, NAGA, SLCA17A5, and LAL (LIPA).

In some embodiments, the hydrophilic peptide comprises between about 2 and about 20 contiguous hydrophilic amino acid residues. In some embodiments, the hydrophilic peptide consists of 2, 4, 8, 12, 16 or 20 hydrophilic amino acid residues. In some embodiments, each hydrophilic amino acid residue is independently selected from the group consisting of lysine, arginine, aspartic acid and glutamic acid. In some embodiments, each hydrophilic amino acid residue of the peptide is the same.

In some embodiments, the blood brain barrier (BBB) receptor targeting agent is a receptor binding domain of an apolipoprotein, or the transferring-receptor binding site of a transferrin. In some embodiments, the BBB receptor targeting agent is the receptor binding domain of an apolipoprotein, wherein the apolipoprotein is selected from the group consisting of: ApoA, ApoB, ApoC, ApoD, ApoE, ApoE2, ApoE3, and ApoE4. In some embodiments, the BBB agent is ApoE.

In some embodiments, the targeting composition comprises at least 8 contiguous lysine residues covalently linked to ApoE. In some embodiments, the targeting composition comprises between 8 and 20 contiguous lysine residues covalently linked to ApoE. In some cmbodiiments, the targeting composition comprises 16 contiguous lysine residues covalently linked to ApoE (e.g., K16ApoE). In some embodiments, the targeting composition is represented by SEQ ID NO: 17.

In some embodiments, the administration of the nucleic acid and the targeting composition is each independently selected from the group consisting of: intravenous administration, intravascular administration, intra-arterial administration, intracerebral administration, intraventricular administration, and intrathecal administration.

In some embodiments, the dose of the nucleic acid (e.g., viral vector containing a nucleic acid) ranges from about $10^9$ genome copies to about $10^{12}$ genome copies. In some embodiments, the dose of targeting composition ranges from about 0.48 μmol/kg to about 1.9 μmol/kg.

In some embodiments, administration of the nucleic acid (e.g., viral vector containing a nucleic acid) and the targeting composition results in increased transduction of CNS tissue relative to administration of the viral vector alone.

In some embodiments, administration of the nucleic acid (e.g., viral vector containing a nucleic acid) and the targeting composition results in increased expression of the transgene in CNS tissue relative to administration of the viral vector alone. In some embodiments, the expression of the transgene is increased at least 10-fold, at least 20-fold, at least 50-fold, at least 100-fold, at least 500-fold, at least 1000-fold, or up to 5000-fold.

In some embodiments, administration of the nucleic acid (e.g., viral vector containing a nucleic acid) and the targeting composition results in expression of the transgene in neurons, neuroglial cells, or neurons and neuroglial cells.

In some embodiments, methods described herein further comprise the step of administering an effective amount of an inhibitor of endocytosis to the subject. In some embodiments, the inhibitor of endocytosis is a small molecule. In some embodiments, the inhibitor of endocytosis is chloroquine, hypertonic sucrose, chlorpromazine, monodansyleadaverine, phenylarsine oxide, monensin, a phenolthiazine compound, methyl-β-cyclodextrin, filipin, cytochalasin D, latrunculin, amiloride, dynasore, dynole, dyngoe, or Pitstop 2.

In some aspects, the disclosure provides a kit comprising (i) a container housing a nucleic acid encoding a transgene; (ii) a container housing a targeting composition, wherein the targeting composition comprises a hydrophilic peptide between 4 and 50 amino acids in length linked to a blood brain barrier (BBB) receptor targeting agent; (iii) an injection device. In some embodiments, the nucleic acid (e.g., viral vector containing a nucleic acid) and the targeting composition are housed in the same container (e.g., housed as a composition comprising a viral vector and a targeting composition, as described herein). In some embodiments, the container housing the viral vector, the container housing the targeting agent, and/or the container housing the composition is a syringe. In some embodiments, the injection device comprises a syringe.

Each of the features of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

FIGS. 1A-1D show Fluc expression in samples obtained from several locations in the brains (anterior to posterior) of mice injected with AAV9-Fluc. FIG. 1E shows Fluc expression in the cerebellum. FIG. 1F shows Fluc expression in the spinal cord. FIGS. 1G-1J show genome copy (gc) of AAV9-Fluc in samples obtained from several locations in the brains (anterior to posterior) of mice injected with AAV9-Fluc. FIG. 1K shows genome copy (gc) of AAV9-Fluc in the cerebellum. FIG. 1L shows genome copy (gc) of AAV9-Fluc in the spinal cord.

FIG. 3A shows increased transgene expression when AAV9 is co-administered with K16ApoE; increased expression is dose dependent. FIG. 3B shows enhancement in transgene expression is modest if AAV9 is infused 15 min prior to 48 nmol of K16ApoE.

FIGS. 4A-4B show enhanced expression in the forebrain. FIGS. 4C-4D show enhanced expression in the midbrain. FIGS. 4E-4F show enhanced expression in the cerebellum and brain stem. FIGS. 4G-4H show enhanced expression in the spinal cord.

FIGS. 5A-5N show systemic co-infusion of scAAV9-CB-GFP with K16ApoE results in efficient neuronal transduction throughout the central nervous system. FIGS. 5A-5B show efficient neuronal transduction in the motor cortex. FIGS. 5C-5D show efficient neuronal transduction in the somatosensory cortex. FIGS. 5E-5F show efficient neuronal transduction in the striatum. FIGS. 5M-5N show efficient neuronal transduction in the ventral horn of the spinal cord.

DETAILED DESCRIPTION

Figures 1A, 1B, 1C, 1D, 1G, 1H, 1I, 1J:
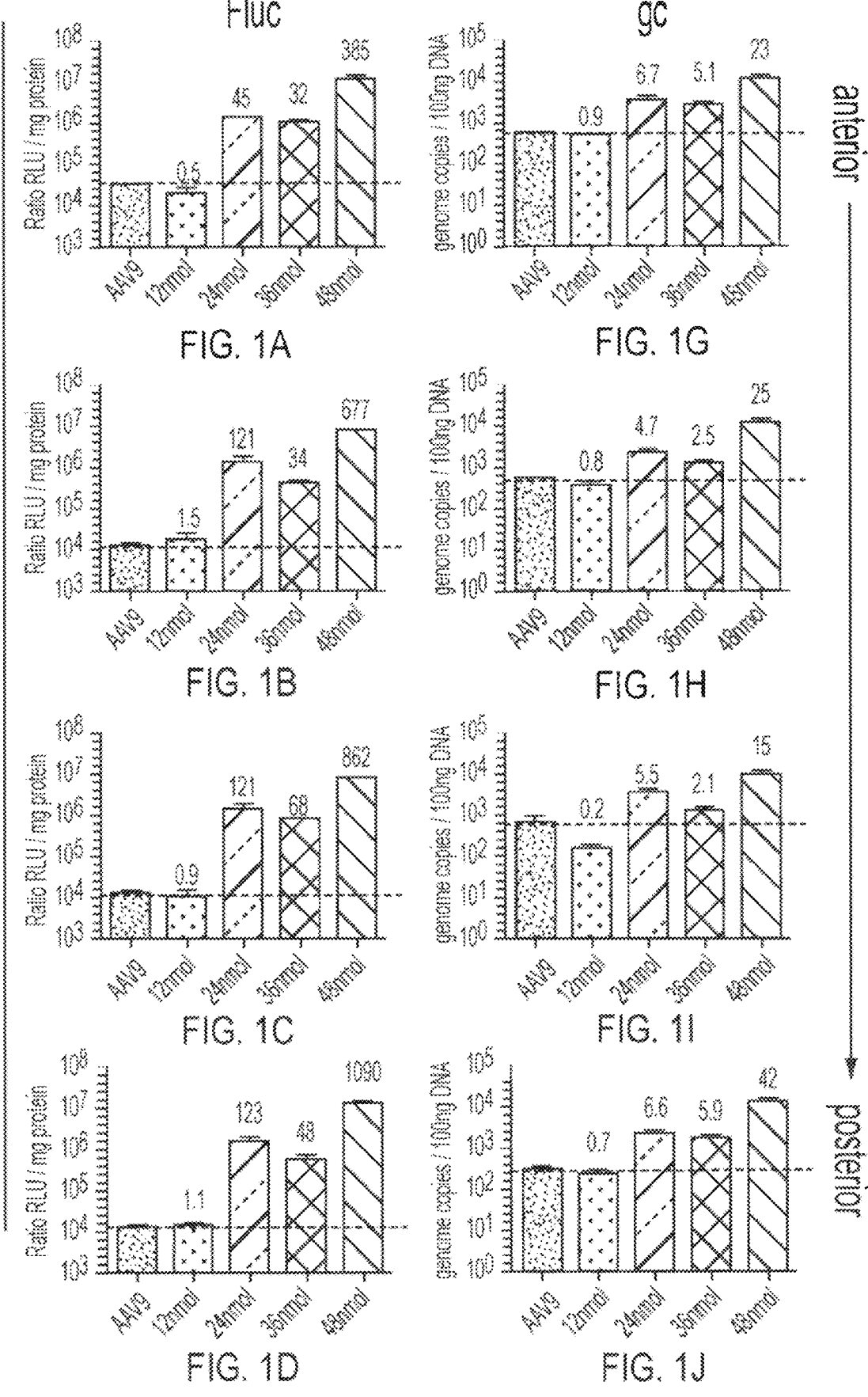
FIGS. 1A-1L show quantification of firefly luciferase (Fluc) expression and genome copy (gc) in the CNS of mice co-injected with varying doses of K16ApoE and AAV9-Fluc.
Figures 1E, 1F, 1K, 1L:
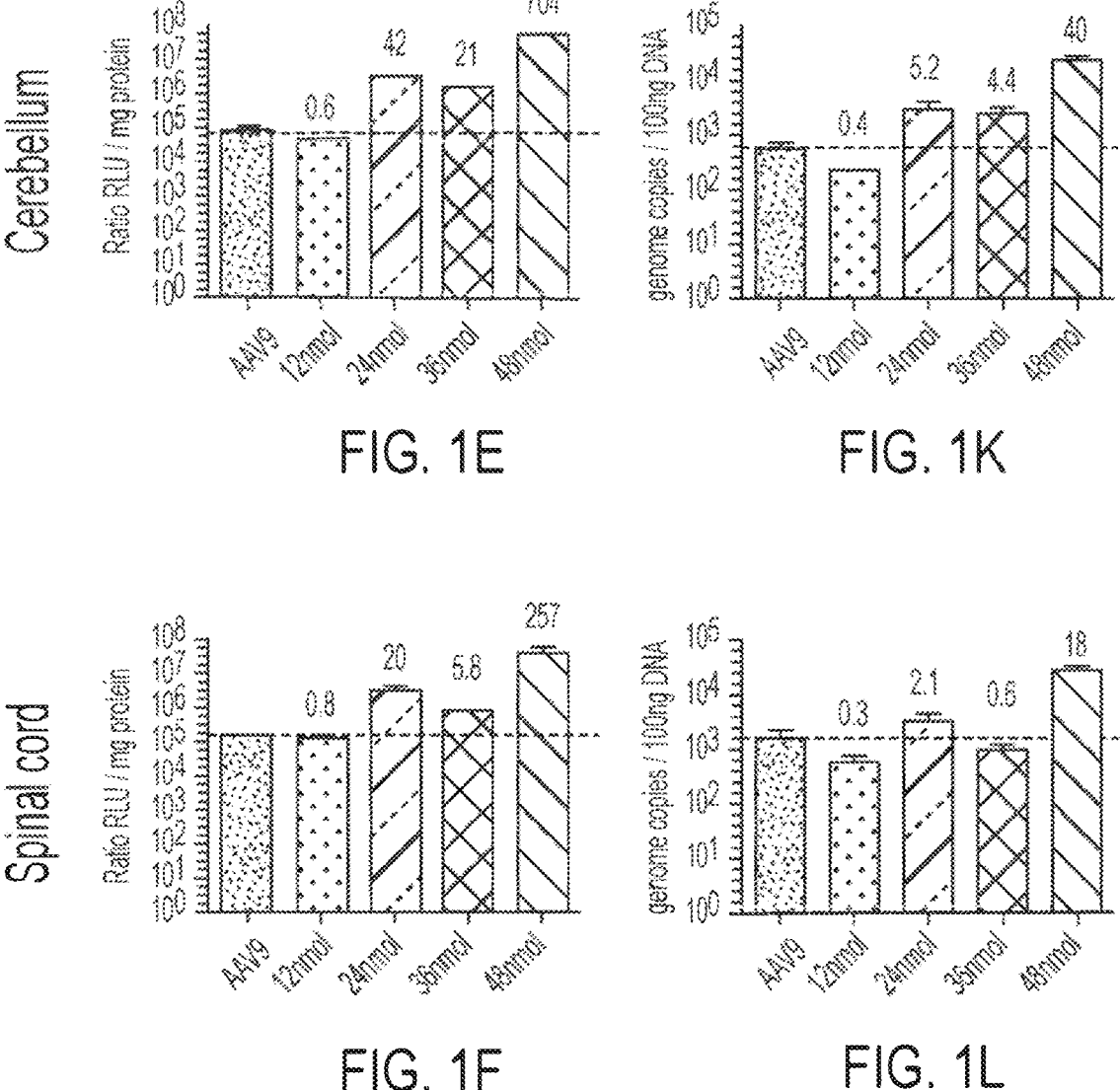

Aspects of the invention relate to the surprising discovery that delivery of nucleic acids (e.g., nucleic acids contained within a viral vector, such as a lentiviral vector or a rAAV) to the CNS of a subject can be enhanced by administering the nucleic acids with a composition comprising a highly hydrophilic molecule conjugated to a blood brain barrier (BBB)-receptor ligand (e.g., K16ApoE). Accordingly, methods and compositions described by the disclosure are useful, in some embodiments, enhancing delivery of transgenes to the CNS of a subject. In some embodiments, methods and compositions described herein are useful for the treatment of CNS diseases (e.g., Huntington's disease, amyotrophic lateral sclerosis, lysosomal storage diseases).

Compositions and Methods for Enhanced Delivery of Transgenes to CNS Tissue

Compositions for enhancing delivery of transgenes to CNS tissue are provided herein. The compositions typically comprise (i) a nucleic acid for expressing a transgene and (ii) a targeting composition comprising a hydrophilic peptide between 4 and 50 amino acids in length linked to a blood brain barrier (BBB) receptor targeting agent.

Aspects of the invention relate to compositions that facilitate the delivery of nucleic acids across the blood brain barrier (BBB). The BBB is a highly selective permeable barrier, formed by endothelial cells of the central nervous system (CNS), that separates circulating blood from the brain extracellular fluid (BECF) in the CNS. Several types of receptors facilitate transport of molecules across the BBB. As used herein, "blood brain barrier (BBB) receptor targeting agent" refers to a peptide or polypeptide that binds (e.g., functions as a ligand) to a receptor located at the blood brain barrier (BBB) and facilitates transport of a biologically active molecule (e.g., a nucleic acid) across the BBB. Examples of BBB receptors that can be targeted by BBB receptor targeting agents described by the disclosure include, but are not limited to, transferrin receptor (TfR), insulin receptor (IR, such as human insulin receptor HIR), insulin-like growth factor receptor (IGF), low density lipoprotein receptor (e.g., LRP1, LRP2, LDLR, VLDLR, Apoer2, LRP4, megalin, and diphtheria toxin receptor, as described in Jones et al., Pharm. Res. 2007, September; 24(9): 1759-1771.

In some embodiments, a blood brain barrier targeting agent comprises a ligand (or receptor binding domain of a ligand) that binds to a low density lipoprotein receptor-related protein (e.g., LRP1, LRP2, or LRP1 and LRP2). Examples of ligands that bind to a low density lipoprotein receptor-related proteins include, but are not limited to, apolipoprotein (ApoA, ApoB, ApoC, ApoD. ApoE. ApoE2, ApoE3, and ApoE4), β-VLDL, lipoprotein lipase, aprotinin, thrombin, anti-thrombin III, C1s/C1q inhibitor, matrix metallopoteinase 9 (MMP-9), fibronectin, receptor-associated protein (RAP), HIV Tat protein, platelet-derived growth factor (PDGF), insulin, connective tissue growth factor (CTGF), and saposin. Further examples of ligands that bind to members of the LDLR family of receptors are described, for example, in Strickland et al., 2002. TRENDS in Endocrinol. & Metab. 11:66-74. In some embodiments, a blood brain barrier targeting agent comprises a receptor binding domain of an apolipoprotein (e.g., ApoE) or a transferrin receptor binding domain of a transferrin receptor.

The disclosure is based, in part, on the recognition that a peptide comprising a contiguous stretch of hydrophilic amino acids (also referred to as a "hydrophilic peptide") linked to a BBB receptor targeting agent increases the efficiency of nucleic acid delivery across the blood brain barrier. Hydrophilic amino acids generally include lysine, arginine, aspartic acid and glutamic acid. However, in some embodiments, a hydrophilic amino acid is selected from the group consisting of arginine, asparagine, aspartic acid, glutamic acid, glutamine, histidine, lysine, serine, threonine, tyrosine, and combinations and unnatural derivatives thereof. In some embodiments, each amino acid of a hydrophilic peptide is independently selected from the group consisting of lysine, arginine, aspartic acid and glutamic acid. In some embodiments, a hydrophilic peptide comprises the same amino acid residue at each position (e.g., consists of a single type of amino acid). In some embodiments, a hydrophilic peptide consists of lysine (K) residues.

In some embodiments, a peptide comprises (or consists of) between about 2 and about 100 contiguous hydrophilic amino acid residues. In some embodiments, a peptide comprises (or consists of) between about 2 and about 50 contiguous hydrophilic amino acid residues. In some embodiments, a peptide comprises (or consists of) between about 4 and about 50 contiguous hydrophilic amino acid residues. In some embodiments, a peptide comprises (or consists of) between about 2 and about 25 contiguous hydrophilic amino acid residues. In some embodiments, a peptide comprises (or consists of) between about 2 and about 20 contiguous hydrophilic amino acid residues. In some embodiments, a peptide comprises (or consists of) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 contiguous hydrophilic amino acid residues.

In some embodiments, a hydrophilic peptide consists of 2, 4.8, 12, 16 or 20 hydrophilic amino acid residues. In some embodiments, a hydrophilic peptide comprises between 8 and 20 contiguous lysine residues. In some embodiments, a hydrophilic peptide consists of 8, 9, 10, 11, 12, 13, 14, 15, 16, 17, 18, 19, or 20 contiguous lysine residues. In some embodiments, a hydrophilic peptide comprises at least 8 contiguous lysine residues. In some embodiments, a hydrophilic peptide comprises or consists of a sequence selected from the group consisting of KK (K2), KKKK (K4; SEQ ID NO: 18). KKKKKKKK (K8; SEQ ID NO: 19), KKKKKKKKKKKK (K12; SEQ ID NO: 20), KKKKKKKKKKKKKKKK (K16; SEQ ID NO: 21), and KKKKKKKKKKKKKKKKKKKK (K20; SEQ ID NO: 22).

In some embodiments, a targeting composition comprises a hydrophilic peptide comprising (or consisting of) at least 8 contiguous lysine residues covalently linked to a BBB receptor targeting agent comprising (or consisting of) a receptor binding portion of ApoE. In some embodiments, a targeting composition comprises a hydrophilic peptide comprising (or consisting of) between 8 and 20 contiguous lysine residues covalently linked to a BBB receptor targeting agent comprising (or consisting of) a receptor binding portion of ApoE. In some embodiments, a targeting composition comprises a hydrophilic peptide comprising (or consisting of) sixteen contiguous lysine residues (K16; SEQ ID NO: 21) linked to a BBB receptor targeting agent comprising (or consisting of) a receptor binding portion of ApoE (SEQ ID NO: 23) and is referred to as "K16ApoE" (SEQ ID NO: 17).

In some aspects, the disclosure provides compositions that facilitate the delivery of a transgene (e.g., a nucleic acid encoding a transgene) across the blood brain barrier (BBB). Generally, a nucleic acid encoding a transgene is delivered via a vector. As used herein, a "vector" refers to a construct which is capable of delivering, and, in some embodiments, expressing, one or more transgenes of interest in a host cell. Non-limiting examples of delivery vectors include viral vectors, nucleic acid expression vectors, naked DNA, and certain eukaryotic cells (e.g., producer cells). In some embodiments, nucleic acids described by the disclosure are delivered via a viral vector. Examples of viral vectors include retroviral vectors (e.g., Maloney murine leukemia virus. MML-V), adenoviral vectors (e.g., AD100), lentiviral vectors (e.g., HIV and FIV-based vectors), and herpesvirus vectors (e.g., HSV-2), as described by Chira et al., Onco-target, 2015, 6(31); 30673-30703. In some embodiments, nucleic acids described by the disclosure are delivered by an adeno-associated virus (AAV) vector (e.g., a recombinant AAV (rAAV) vector). rAAV vectors are described in further detail elsewhere in the disclosure.

In some cases, it is desirable to limit the amount of a nucleic acid (e.g., a nucleic acid delivered by a vector) that crosses the blood brain barrier of a subject. One strategy for limiting the transport of molecules across the blood brain barrier is to interfere with the endocytic pathway. Accordingly, in some embodiments, compositions described by the disclosure comprise an inhibitor of endocytosis. As used herein, "inhibitor of endocytosis" refers any agent that inhibits or abrogates by any means endocytosis or internalization of a ligand by a blood brain barrier cell. An inhibitor of endocytosis can be a small molecule, peptide or poly-peptide (e.g., dynamin peptide), antibody (e.g., anti-clathrin antibody), or interfering RNA molecule (e.g., RNAi molecule targeting endocytic pathway proteins, for example clathrin heavy chain, flotillin-1, caveolin-1, dynamin-2 and Pak-1). Non-limiting examples of small molecule endocytosis inhibitors include methyl-p-cyclodextrin (μ-CD), hydrophobic amines (such as phenothiazines, monodansyl-cadaverine, chloroquine), monensin, hyperosmotic sucrose and dynasore. Phenothiazines include, but are not limited to, chlorpromazine, fluphenazine, mesoridazine, perphenazine, prochlorperazine, promazine, thioridazine, trifluoperazine and triflupromazine. Additional examples of endocytosis inhibitors are disclosed, for example in Dutta et al., Cell Logist., 2012, Oct. 1; 2(4); 203-208.

Methods for enhancing delivery of transgenes to CNS tissue are provided herein. The methods typically involve administering to a subject (i) an effective amount of a viral vector comprising a nucleic acid for expressing a transgene and (ii) a targeting composition comprising a hydrophilic peptide covalently linked to a blood brain barrier (BBB) agent.

Recombinant Adeno-Associated Viruses (rAAVs)

In some aspects, nucleic acids described by the disclosure are delivered by an isolated AAV vector. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more prede-termined tissue(s) (e.g., CNS tissue). The AAV capsid is an important element in determining these tissue-specific tar-geting capabilities. Thus, an rAAV having a capsid appro-priate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodi-ments, the functions of the capsid proteins are to protect the viral genome, deliver the genome and interact with the host. In some aspects, capsid proteins deliver the viral genome to a host in a tissue specific manner.

Generally, the capsid protein of a viral vector described by the disclosure can be a capsid protein having any AAV serotype (e.g., AAV1, AAV2, AAV3, AAV4, AAV5, AAV6, AAV7, AAV8. AAV9, AAV10, AAVrh.8, AAVrh.10, AAV.rh39, AAVrh.43, and variants thereof). In some embodiments, an AAV capsid protein is of an AAV serotype selected from the group consisting of AAV1, AAV2, AAV2i8, AAV2.5, AAV6, AAV8, AAVrh8, AAV9, AAVrh10, AAV-B1, AAV9.45, AAV9.45AS, 9.45-Angiopep, AAV9.47-Angiopep, and AAV9.47-AS. In some embodi-ments, an AAV capsid protein is of a serotype derived from a non-human primate (e.g., AAVrh8. AAVrh10). In some embodiments, an AAV capsid protein is represented by the sequence set forth in any one of SEQ ID NO: 1-14.

In some embodiments, an AAV capsid protein comprises a heterologous targeting peptide, for example as described by International Patent Application No. PCT/US2015/053798, filed Oct. 2, 2015, the entire content of which is incorporated herein by reference. A heterologous targeting peptide can be located at the N-terminus or the C-terminus of an AAV capsid protein. In some embodiments, a heter-ologous targeting peptide is represented by the formula $[A]_n$, wherein A is alanine and n is an integer in a range of 5 to 31. For example, in some embodiments, a heterologous target-ing peptide is represented by AAAAAAAAAAAAAAAAAAAA (SEQ ID NO: 16). In some embodiments, a heterologous targeting peptide is a lipoprotein receptor-related protein (LRP) ligand, for example Angiopep-2 (or a fragment thereof). In some embodiments, a heterologous targeting peptide comprises (or consists of) the amino acid sequence TFFYGGSRGKRNNFKTEEY (SEQ ID NO: 1.5). In some embodiments, an AAV capsid protein having a heterologous targeting peptide is of an AAV9, optionally AAV9.45 or AAV9.47, serotype.

In some embodiments, an AAV capsid protein is a chimeric AAV capsid protein, for example as described in International Patent Application PCT/2015/053804, filed Oct. 2, 2015, the entire contents of which are incorporated herein by reference. In some embodiments, the chimeric AAV capsid protein comprises distinct polypeptide regions derived from at least two, at least three, at least four, at least five or more different AAV serotypes selected from the group consisting of: AAV1, AAV2, AAV4, AAV5, AAV6. AAV8. AAV9, AAVrh.8, AAVrh.10. AAVrh.39, and AAVrh.43. In some embodiments, the chimeric AAV capsid protein comprises distinct polypeptide regions of greater than four, greater than five, greater than six, greater than seven or more amino acids in length that are derived from different AAV serotypes (e.g., at least two) selected from the group consisting of: AAV1. AAV2, AAV4. AAV5, AAV6, AAV8. AAV9, AAVrh.8, AAVrh.10. AAVrh.39, and AAVrh.43. In some embodiments, an AAV capsid protein is represented by any one of SEQ ID NO: 1-14.

In some embodiments, an rAAV comprises at least two different capsid proteins, for example a first capsid protein of a first serotype and a second capsid protein of a second serotype, or having a wild type capsid protein of a particular serotype and a mutant capsid protein of the same serotype. In some embodiments, such rAAV are referred to as "multiplex rAAV" or "mosaic rAAV". Examples of multiplex rAAV are generally described, for example, by Choi et al., Curr Gene Ther. 2005 June; 5(3): 299-310.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a CNS-associated transgene (e.g., ASPA). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual. Cold Spring Harbor Press. Cold Spring Harbor, N.Y. Similarly, methods of generating rAAV virions are well known and the selection of a suitable method is not a limitation on the present disclosure. See. e.g., K. Fisher et al. J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing. AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See. e.g., Graham et al. (1973) Virology, 52:456. Sambrook et al. (1989) Molecular Cloning, a laboratory manual. Cold Spring Harbor Laboratories. New York. Davis et al. (1986) Basic Methods in Molecular Biology. Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of a viral vector. (e.g., a lentiviral vector, retroviral vector), an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned." "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods. e.g., Molecular Cloning: A Laboratory Manual, J. Sambrook, et al., eds., Second Edition, Cold Spring Harbor Laboratory Press. Cold Spring Harbor. New York, 1989, or Current Protocols in Molecular Biology. F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene. In some embodiments, the transgene is a CNS-associated transgene. In some embodiments, a rAAV vector further comprises nucleic acid sequences encoding one or more AAV inverted terminal repeat sequences (ITRs), for example AAV2 ITRs.

The AAV sequences of the vector typically comprise the cis-acting 5' and 3' inverted terminal repeat sequences (See, e.g., B. J. Carter, in "Handbook of Parvoviruses", ed., P. Tijsser, CRC Press. pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein. "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains.

Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan. M D et al., EMBO, 1994; 4: 928-933; Mattion, N M et al., J Virology. November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary. 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al. Cell, 41:521-530 (1985)], the SV40 promoter, the dihydrofolate reductase promoter, the β-actin promoter, the phosphoglycerol kinase (PGK promoter, and the EF1α promoter [Invitrogen]. In some embodiments, a promoter is an enhanced chicken μ-actin promoter.

Inducible promoters allow regulation of gene expression and can be regulated by exogenously supplied compounds, environmental factors such as temperature, or the presence of a specific physiological state. e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA. 93:3346-3351 (1996)), the tetracycline-repressible system (Gossen et al. Proc. Natl. Acad. Sci. USA. 89:5547-5551 (1992)), the tetracycline-inducible system (Gossen et al, Science, 268:1766-1769

(1995), see also Harvey et al. Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter. Arbuthnot et al., Hum. Gene Ther., 7:1503-14 (1996)), bone osteocalcin promoter (Stein et al., Mol. Biol. Rep., 24:185-% (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter, T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al. Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Transgenes

In some aspects, the disclosure relates to methods and compositions for treating CNS-related disorders. As used herein, a "CNS-related disorder" is a disease or condition of the central nervous system. A CNS-related disorder may affect the spinal cord (e.g., a myelopathy), brain (e.g., a encephalopathy) or tissues surrounding the brain and spinal cord. A CNS-related disorder may be of a genetic origin, either inherited or acquired through a somatic mutation. A CNS-related disorder may be a psychological condition or disorder, e.g., Attention Deficient Hyperactivity Disorder. Autism Spectrum Disorder, Mood Disorder. Schizophrenia, Depression. Rhett Syndrome, etc. A CNS-related disorder may be an autoimmune disorder. A CNS-related disorder may also be a cancer of the CNS, e.g., brain cancer. A CNS-related disorder that is a cancer may be a primary cancer of the CNS, e.g., an astrocytoma, glioblastomas, etc., or may be a cancer that has metastasized to CNS tissue, e.g., a lung cancer that has metastasized to the brain. Further non-limiting examples of CNS-related disorders, include Huntington's disease, Parkinson's Disease, Lysosomal Storage Disease, Ischemia. Neuropathic Pain. Amyotrophic lateral sclerosis (ALS), Multiple Sclerosis (MS), Canavan disease (CD), frontotemporal lobar degeneration (FTLD), spinocerebellar ataxias, spinal and bulbar muscular atrophy, dentatorubropallidoluysian atrophy, and Freiderich's ataxia.

In some embodiments, the disclosure relates to a nucleic acid encoding a protein or functional RNA useful for the treatment of a condition, disease or disorder associated with the central nervous system (CNS). The following is a non-limiting list of genes associated with CNS disease: DRD2, GRIA1, GRIA2, GRIN1, SLClA1, SYP, SYT1, CHRNA7, 3Rtau/4r TUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; huntingtin (Htt), IT15, PRNP, JPH3, TBP, ATXN1, ATXN2, ATXN3, Atrophin 1, FTL, TITF-1, Xbp1s, CRAG, associated with Huntington's Disease; FXN, associated with Freidrich's ataxia; ASPA, associated with Canavan's Disease; DMD, associated with muscular dystrophy; SMN1, UBE 1, DYNC1H1 associated with spinal muscular atrophy; ALS2, ANG, ATXN2, C9orf72, DCTN1, FIG4, FUS, NEFH, OPTN, PFN1, PRPH, SETX, SIGMAR1, SMN1, SOD1, SPG11, TARDBP, UBQLN2, VAPB, VCP, associated with amyotrophic lateral sclerosis (ALS); MAN2B1. MAN2B2, MAN2C1, associated with Alpha-Mannosidosis; AGA, associated with Aspartylglucosaminuria; CLN1. CLN2, CLN3, CLN5, CLN6, MFSD8, CLN8, CTSD, associated with Batten disease; MANBA, associated with Beta-Mannosidosis; CTNS, associated with cystinosis; LAMP2, associated with Danon disease; GLA, associated with Fabry disease; ASAH1, associated with Farber disease; FUCA1, associated with fucosidosis; CTSA, associated with Galactosialidosis; GBA, associated with Gaucher disease; GALC, associated with Krabbe disease; ARSA, associated with metachromic leukodystrophy; and IDUA, DS, SGSH, NAGLU, HGSNAT, GNS, GALNS, ARSB, GUSB, HYAL1, SMPD1, NPC1, NPC2, GAA, NAGA, SLCA17A5, and LAL (LIPA), associated with Mucopolysaccharidosis disorders (e.g., Hurler syndrome, Hunter syndrome, Sanfilippo A-D, Morquio, hyaluronidase deficiency, Maroteaux-Lamy, Sly syndrome, sialidosis, I-cell disease, mucolipidosis types I-IV, multiple sulfatase deficiency, Niemann-Pick types A-C, Pompe disease, Pycnodysostosis, Sandhoff disease, Schlinder disease, Tay-Sachs, Wolman disease).

Useful transgene products also include miRNAs. miR-NAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides. TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-mi R-1306, hsa-mi R-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-2(4, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-MiR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-30.1a, hsa-miR-301b, hsa-miR-302a, hsa-miR-302a*, hsa-miR-302b, hsa-miR-302b*, hsa-miR-302c, hsa-miR-302e*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR- 346, hsa-miR-34a, hsa-miR-34a*, hsa-miR-34h, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR489, hsa-miR-490-3p, hsa-miR-490-5p, hsa-miR-491-3p, hsa-miR-491-5p, hsa-miR-492, hsa-miR493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518c, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-mi R-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891 b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a rAAV vector, as discussed above. MicroRNA sponges specifically inhibit miRNAs through a complementary heptameric seed sequence (Ebert, M. S. Nature Methods, Epub Aug. 12, 2007). In some embodiments, an entire family of miRNAs can be silenced using a single sponge sequence. TuD RNAs achieve efficient and long-term-suppression of specific miR-NAs in mammalian cells (See, e.g., Takeshi Haraguchi, et al., Nucleic Acids Research, 2009. Vol. 37. No. 6 e43, the contents of which relating to TuD RNAs are incorporated herein by reference). Other methods for silencing miRNA function (derepression of miRNA targets) in cells will be apparent to one of ordinary skill in the art.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

In some aspects, the disclosure provides compositions and methods for efficient delivery of nucleic acids to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

In some aspects, the disclosure relates to methods and compositions that increase transduction efficiency or efficacy of CNS tissue or cells by facilitating transport of molecules (e.g., nucleic acids) across the BBB. In some embodiments, administration of nucleic acids and targeting compositions described by the disclosure results in transductions of neurons, neuroglial cells, or neurons and neuroglial cells. Examples of neurons include, but are not limited to, motor neurons, sensory neurons, pyramidal neurons, Purkinje cells, retinal neurons, olfactory neurons, basket cells, Betz cells, Lugaro cells, spiny neurons (e.g., spiny neurons), Renshaw cells, Granule cells, horn cells, and spindle cells. Examples of neuroglial cells include, but are not limited to, microglia (e.g., amoeboid, ramified, activated non-phagocytic, activated phagocytic, Gitter cells, perivascular cells, juxtavascular), astrocytes, oligodendrocytes, ependymal cells, radial glia, Schwann cells, satellite cells, and enteric glial cells.

Aspects of the instant disclosure relate to compositions comprising a recombinant AAV comprising a capsid protein and a nucleic acid encoding a transgene (e.g., a CNS-associated transgene). In some embodiments, the nucleic acid further comprises AAV ITRs. In some embodiments, a composition further comprises a pharmaceutically acceptable carrier.

The compositions of the disclosure may comprise nucleic acid (e.g., a first viral vector containing a nucleic acid encoding one or more first transgenes) alone, or in combination with one or more other nucleic acids (e.g., a second viral vector having a nucleic acid encoding one or more different transgenes). In some embodiments, a composition comprises 1, 2, 3, 4, 5, 6, 7, 8, 9, 10, or more different nucleic acids each having one or more different transgenes.

Aspects of the disclosure relate to the surprising discovery that administration of a targeting composition (e.g., a targeting composition comprising a hydrophilic peptide between 4 and 50 amino acids in length linked to a blood brain barrier (BBB) receptor targeting agent) facilitates transport of nucleic acids (e.g., viral vectors containing nucleic acids encoding one or more transgenes) across the blood brain barrier and into CNS tissue. Targeting compositions described by the disclosure can be administered to a subject before, concurrently (e.g., co-administered, or administered simultaneously) or after administration of a nucleic acid (e.g., a viral vector containing a nucleic acid encoding a transgene) to a subject.

A targeting composition can be administered to a subject at any appropriate dosage. An appropriate dosage is a dosage at which the targeting composition performs its intended function (e.g., facilitates transport of a nucleic acid across the BBB) without effecting toxicity on the subject. For example, in some embodiments, the dosage of targeting composition administered to a subject (e.g., a mouse) ranges from about 0.48 µmol/kg to about 1.9 µmol/kg. Factors such as solubility, bioavailability, biological half-life, route of administration, product shelf life, as well as other pharmacological considerations will be contemplated by one skilled in the art of preparing such targeting compositions, and as such, a variety of dosages and treatment regimens may be desirable.

In some embodiments, a targeting composition is administered to a subject prior to administration of a nucleic acid (e.g., a viral vector containing a nucleic acid encoding a transgene). A targeting composition can be administered to a subject between 1 hour and 1 second before administration of a nucleic acid to the subject. In some embodiments, a targeting composition is administered to a subject about 30 minutes, 29 minutes, 28 minutes, 27 minutes, 26 minutes, 25 minutes, 24 minutes, 23 minutes, 22 minutes, 21 minutes, 20 minutes, 19 minutes, 18 minutes, 17 minutes, 16 minutes, 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1 minutes, or 0.5 minutes before administration of a nucleic acid to the subject.

In some embodiments, a targeting composition is administered to a subject at the same time (e.g., concurrently or simultaneously) as a nucleic acid. A targeting composition and a nucleic acid can be administered concurrently or simultaneously as a single composition, or as separate compositions.

In some embodiments, a targeting composition is administered to a subject about 30 minutes, 29 minutes, 28 minutes, 27 minutes, 26 minutes, 25 minutes, 24 minutes, 23 minutes, 22 minutes, 21 minutes, 20 minutes, 19 minutes, 18 minutes, 17 minutes, 16 minutes, 15 minutes, 14 minutes, 13 minutes, 12 minutes, 11 minutes, 10 minutes, 9 minutes, 8 minutes, 7 minutes, 6 minutes, 5 minutes, 4 minutes, 3 minutes, 2 minutes, 1 minutes, or 0.5 minutes after administration of a nucleic acid to the subject.

In some embodiments, compositions described by the disclosure comprise a pharmaceutically acceptable carrier. Suitable carriers may be readily selected by one of skill in the art in view of the indication for which the composition (e.g., viral vector, targeting composition) is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the compositions and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors (e.g., rAAVs) am administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intravascular, intra-arterial, intracerebral, intraventricular, intrathecal, intramuscular, subcutaneous, intradermal, intratumoral, and other parental routes of administration. Routes of administration may be combined, if desired.

The dose of virions (e.g., rAAV virions) required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of a viral vector (e.g., a rAAV) is an amount sufficient to target infect an animal, target a desired tissue. In some embodiments, an effective amount of a viral vector (e.g., a rAAV) is an amount sufficient to produce a stable somatic transgenic animal model. The effective amount will depend primarily on factors such as the species, age, weight, health of the subject, and the tissue to be targeted, and may thus vary among animal and tissue. For example, an effective amount of an rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{12}$ or $10^{13}$ rAAV genome copies is effective to target heart, liver, and pancreas tissues. In some embodiments, $10^9$ to about $10^{12}$ rAAV genome copies is effective to target the CNS, when administered with a targeting composition described herein.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants. pH adjustment, salt concentration adjustment, etc. (See. e.g., Wright FR. et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example. "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions (e.g., rAAV-based compositions, targeting compositions) disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein. "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the disclosure relates to a kit comprising a targeting composition and a nucleic acid encoding a transgene. In some embodiments, the nucleic acid encoding a transgene is contained in a viral vector (e.g., a rAAV). In some embodiments, the kit further comprises instructions for transducing CNS tissue.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape. DVD, etc.), Internet. and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See. e.g., U.S. Pat. Nos. 5,871,982 and 6,251,677, which describe a hybrid Ad/AAV virus. A variety of adenovirus stains are available from the American Type Culture Collection, Manassas. Va., or available by request from a variety of commercial and institutional sources. Further, the sequences of many such strains are available from a variety of databases including. e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum scalable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: Administration of AAV9-Fluc and K16ApoE Enhances Transduction Efficiency In some embodiments, vascular infusion of K16ApoE peptide enhances CNS entry of small molecules, antibodies and enzymes. Data provided in this example demonstrate that co-infusion of K16ApoE with AAV9 enhances CNS gene therapy by up to ~1.000-fold.

Vascular infusion of an AAV9 vector with K16ApoE peptide in adult animals enhances CNS gene transfer efficiency by up to 1.000-fold in a dose dependent manner. Enhancement in transgene expression corresponds to increased neuronal transduction throughout the CNS, which addresses a major limitation of systemic administration of current AAV vectors in adult animals, where CNS transduction is mostly restricted to astrocytes and endothelial cells.

Figure 2:
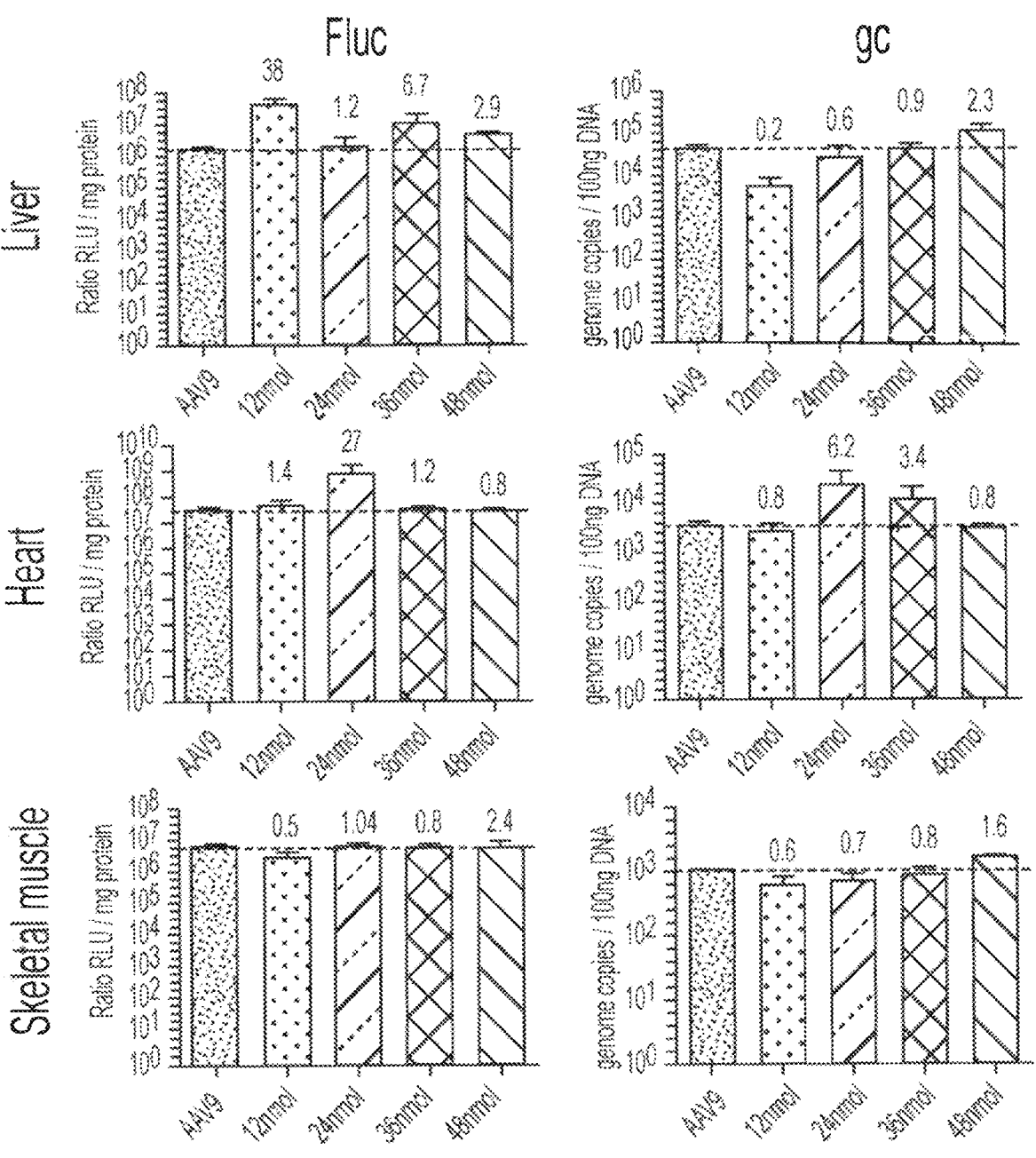
FIG. 2 shows quantification of firefly luciferase (Fluc) expression and genome copy (gc) in the liver, heart and skeletal tissue of mice co-injected with varying doses of K16ApoE and AAV9-Fluc.
Figure 3A:
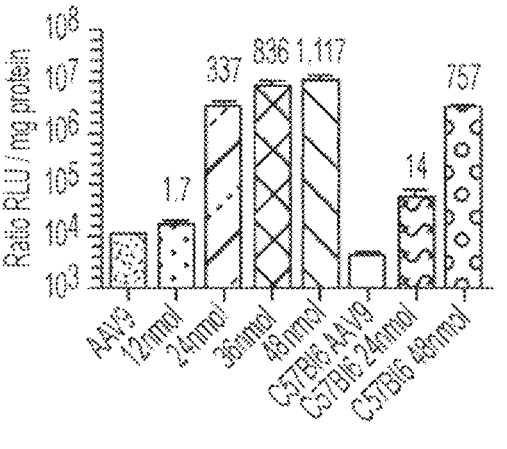
FIGS. 3A-3B show enhancement in transgene expression occurs in C57BL6J mice.

A single stranded AAV9-Fluc vector ($5\times10^{11}$ vg) was infused in 6-8 week old Balb/c mice via the tail vein after pre-incubation with K16ApoE peptide (12, 24, 36, 48 nmol) for 60 min at room temperature. Firefly luciferase (Fluc) expression in the CNS of mice co-injected with K16ApoE and AAV9 was higher than AAV9 alone in a K16ApoE dose dependent manner with a maximum of ~1000-fold differential (FIG. 1A-F). Analysis of vector genome copy content also showed a K16-ApoE dose dependent increase throughout the CNS (FIG. 1G-L). The effect of co-infusion of K16ApoE with AAV9 on transduction of liver, heart and skeletal indicates considerable enhancement at certain lower doses, but relatively small increases in transgene expression (2-3 fold) for 48 nmol K16ApoE (FIG. 2). The experiment in Balb/c mice was repeated with identical results (FIG. 3). Enhancement in transgene expression also occurs in C57BL6J mice (FIG. 3A).

Figure 3B:
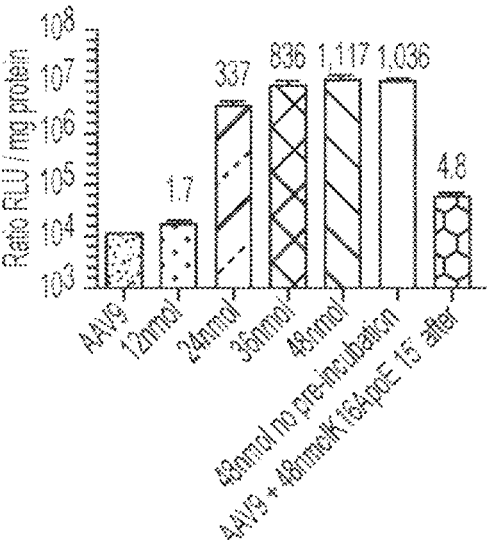

In addition data indicates pre-incubation of K16ApoE with AAV9 is not necessary and that the enhancement in transgene expression is modest if AAV9 is infused 15 min prior to 48 nmol of K16ApoE (FIG. 3B). This latter result indicates either that bioavailable AAV9 in blood is rapidly depleted after vascular infusion, or that the interaction of K16ApoE with AAV9 does not occur as the 48 nmol of K16ApoE is diluted upon infusion into the blood and potentially hinders interaction with AAV9 to a such a degree that no effect is observed.

Figures 4A, 4B, 4C, 4D:
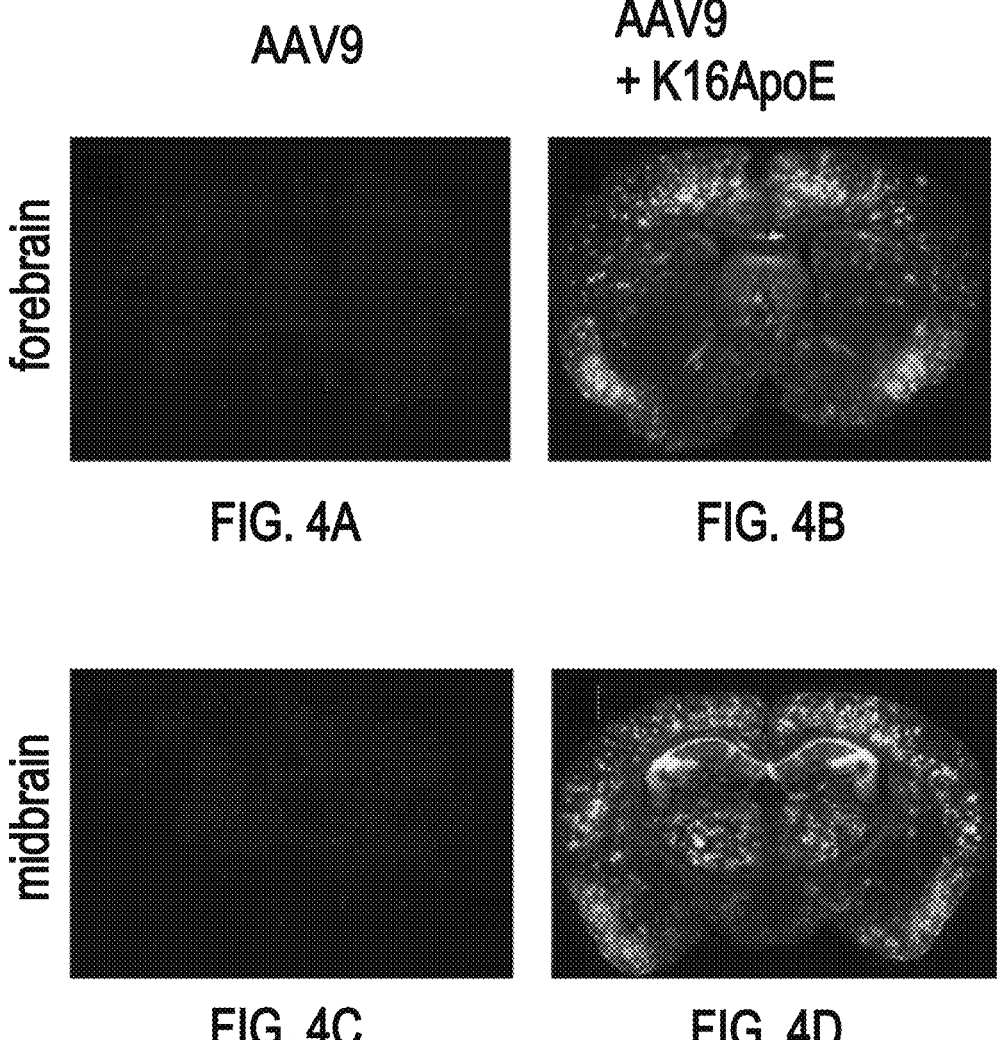
FIGS. 4A-4H show enhancement of transgene expression in central nervous system tissues after systemic co-injection of K16ApoE and AAV9-GFP compared to AAV9-GFP alone.
Figures 4E, 4F, 4G, 4H:
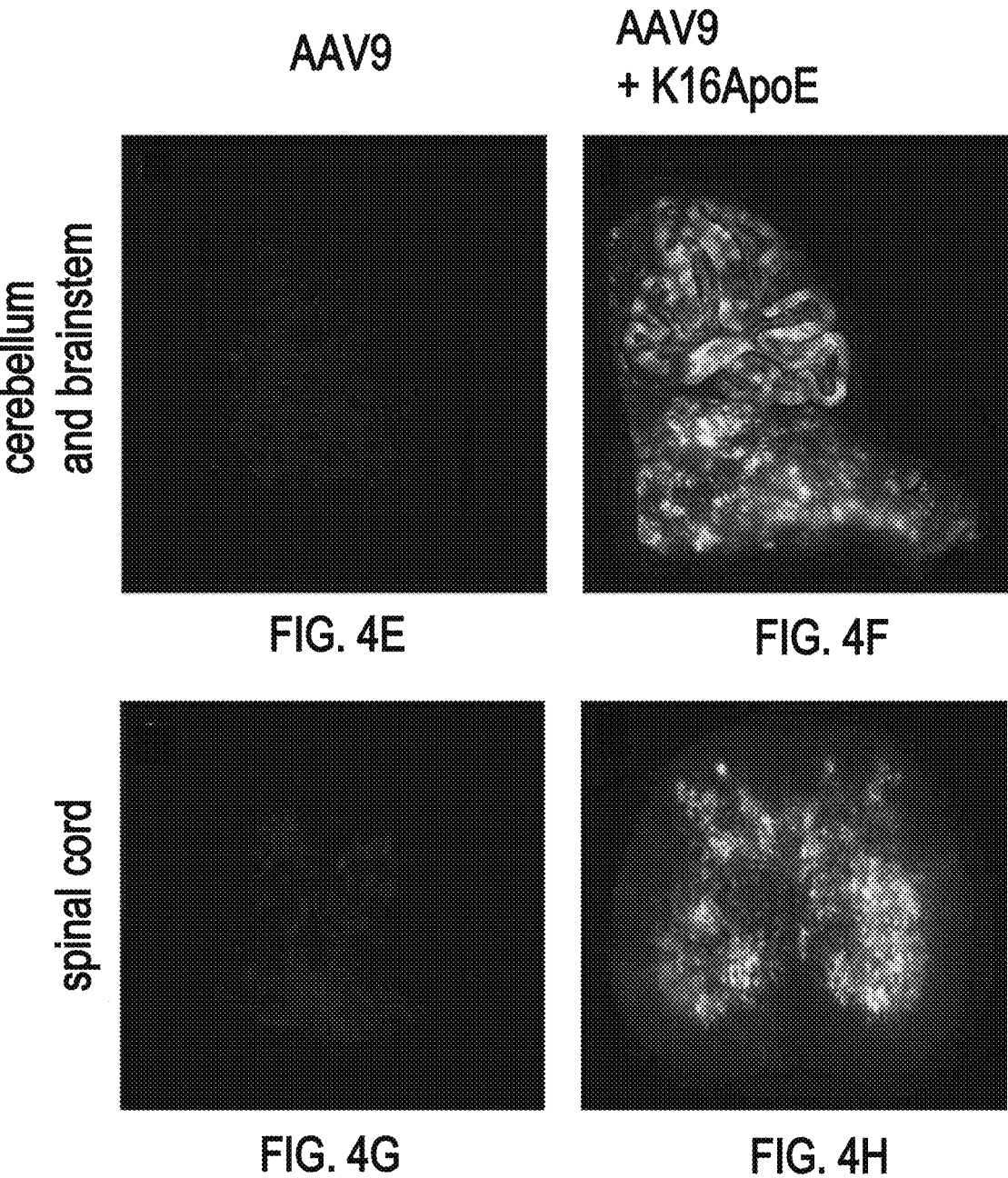

Example 2: Systemic Co-Injection of AAV9 with K16ApoE Enhances Gene Transfer Efficiency Throughout the CNS Six to eight-week old C57BL/6 mice received a systemic infusion of $1\times10^{12}$ vg scAAV9-CB-GFP vector alone or with 48 nmol ApoE-K16 peptide. GFP expression analysis at 4 weeks post-injection showed that co-infusion with ApoE-K16 peptide enhanced the efficiency of gene transfer throughout the CNS. FIGS. 4A-4B show enhanced expression of scAAV9-GFP in the forebrain of mice that were co-administered K16ApoE. FIGS. 4C-4D show enhanced expression in the midbrain where scAAV9-GFP was co-administered with K16ApoE. FIGS. 4E-4F show enhanced expression in the cerebellum and brain stem where scAAV9-GFP was co-administered with K16ApoE. FIGS. 4G-4H show enhanced expression in the spinal cord where scAAV9-GFP was co-administered with K16ApoE.

Figures 5A, 5B, 5C, 5D, 5E, 5F:
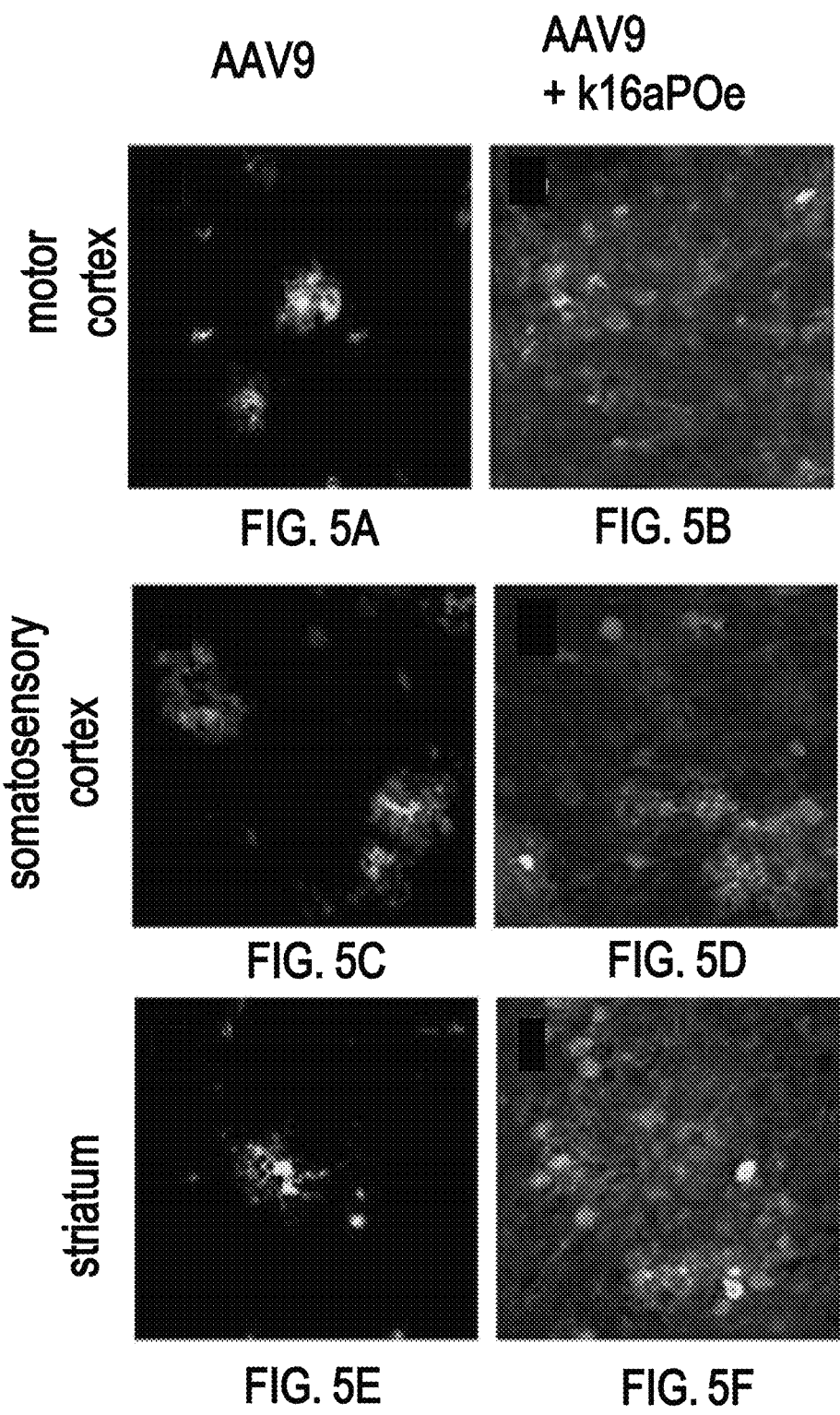
Figures 5G, 5H, 5I, 5J, 5K, 5L:
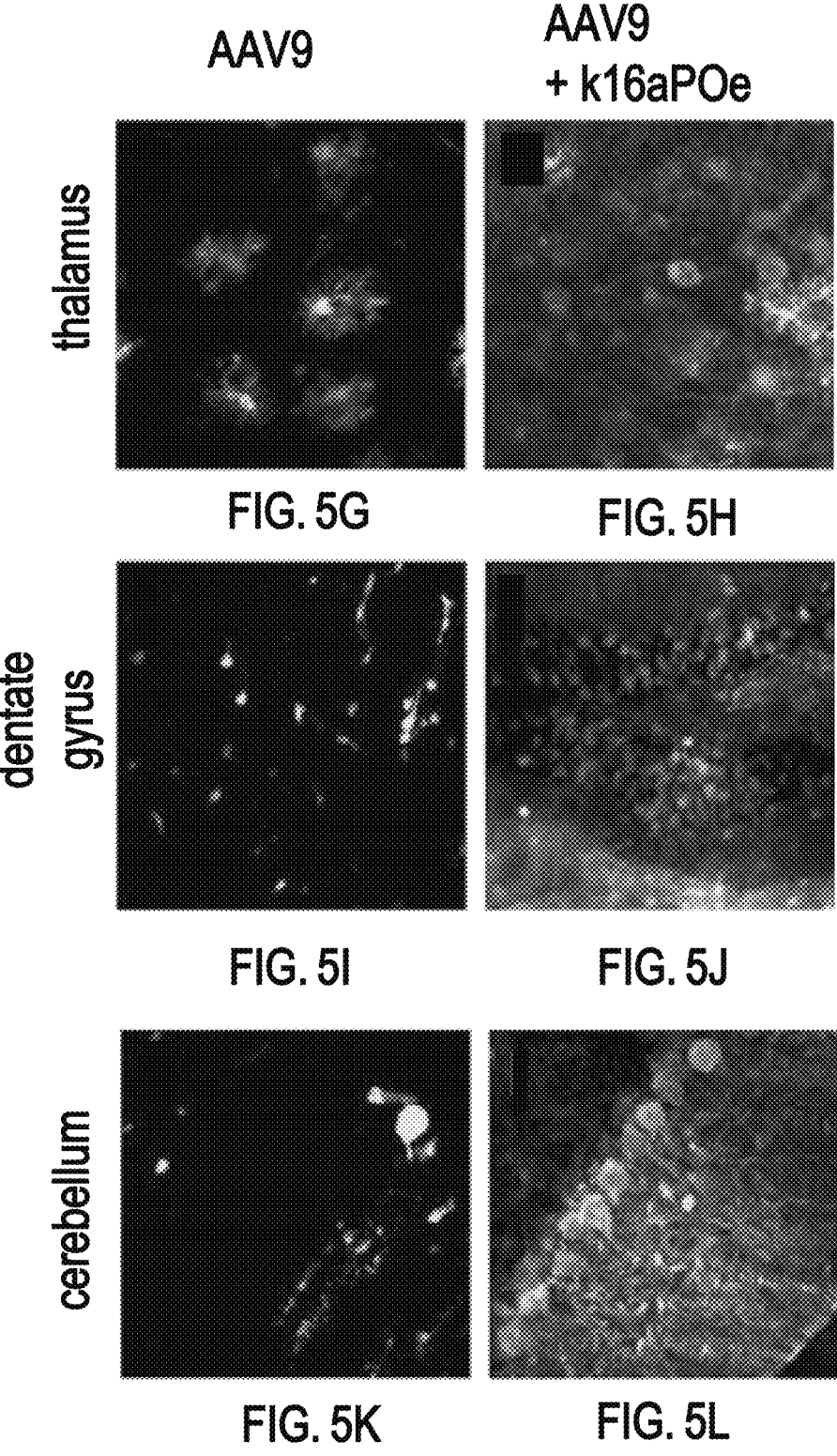
FIGS. 5G-5H show efficient neuronal transduction in the thalamus.
FIGS. 5I-5J show efficient neuronal transduction in the dentate gyrus.
FIGS. 5K-5L show efficient neuronal transduction in the cerebellum.
Figures 5M, 5N:
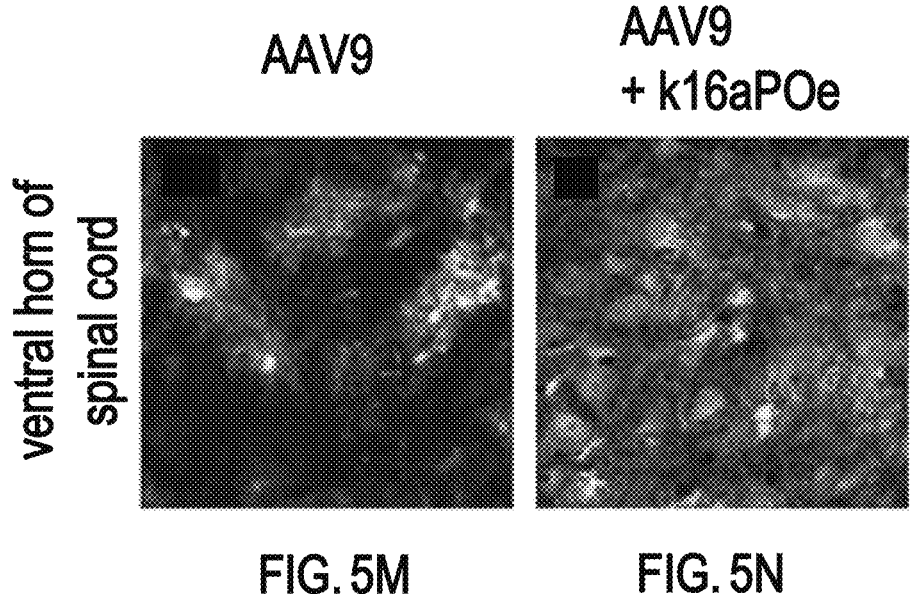

In another set of experiments, six to eight-week old C57BL/6 mice received a systemic infusion of $1\times10^{12}$ vg scAAV9-CB-GFP vector alone or with 48 nmol ApoE-K16 peptide. GFP expression analysis at 4 weeks post-injection showed that co-infusion with ApoE-K16 peptide increased neuronal transduction throughout the CNS. FIGS. 5A-5B show efficient neuronal transduction of scAAV9-CB-GFP in the motor cortex of mice that were co-administered K16ApoE. FIGS. 5C-5D show efficient neuronal transduction of scAAV9-CB-GFP in the somatosensory cortex of mice that were co-administered K16ApoE. FIGS. 5E-5F show efficient neuronal transduction of scAAV9-CB-GFP in the striatum of mice that were co-administered K16ApoE. FIGS. 5G-5H show efficient neuronal transduction of scAAV9-CB-GFP in the thalamus of mice that were co-administered K16ApoE. FIGS. 5I-5J show efficient neuronal transduction of scAAV9-CB-GFP in the dentate gyrus of mice that were co-administered K16ApoE. FIGS. 5K-5L show efficient neuronal transduction of scAAV9-CB-GFP in the cerebellum of mice that were co-administered K16ApoE. FIGS. 5M-5N show efficient neuronal transduction of scAAV9-CB-GFP in the ventral horn of the spinal cord of mice that were co-administered K16ApoE.

Figure 6:
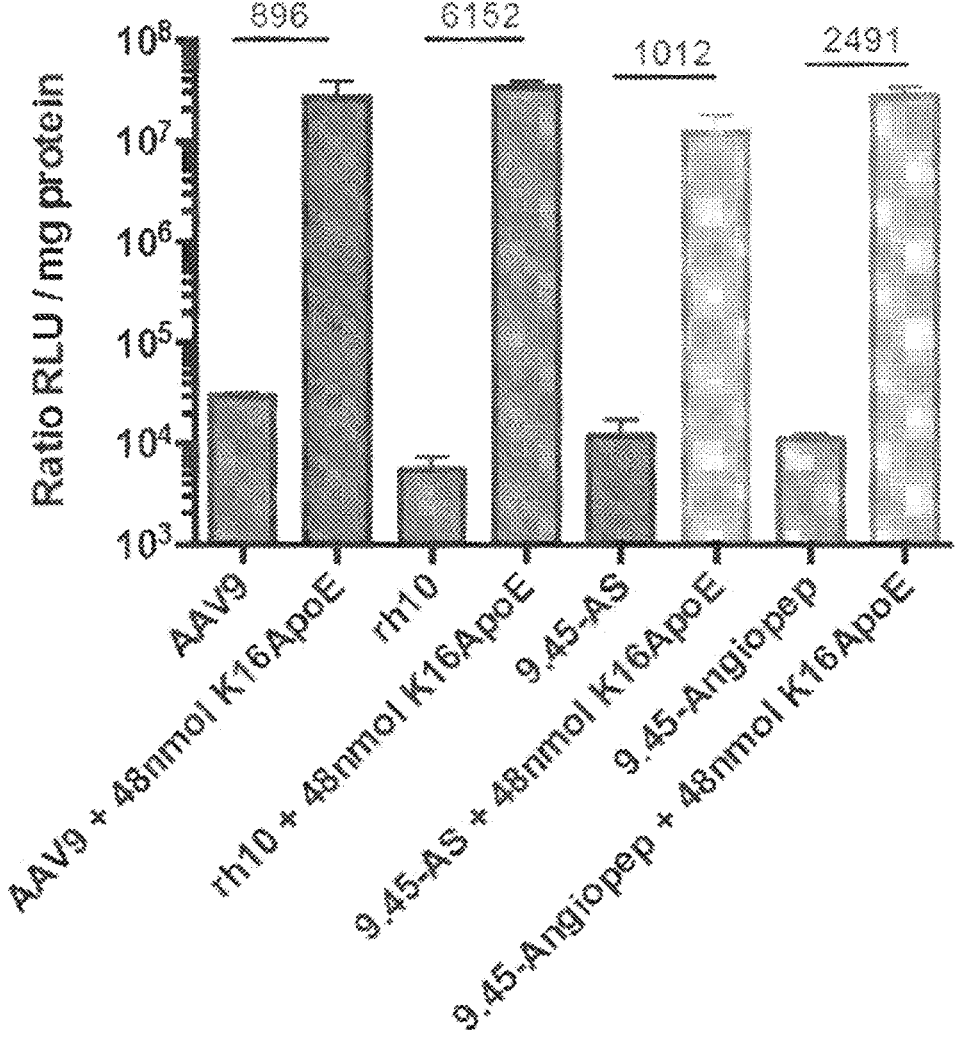
FIG. 6 shows co-injection of K16ApoE enhances CNS gene transfer of different recombinant AAV vectors, such as AAV9, AAVrh.10, AAV9.45-AS, and AAV9.45-Angiopep.

Example 3: Co-Injection of K16ApoE Enhanced CNS Gene Transfer of Different Recombinant AAV Vectors Male Balb/c mice (6-8 week-old; n=4) received a systemic infusion of $5\times10^{11}$ vg of different AAV vectors encoding firefly luciferase (Fluc) via the tail vein with, and without, 48 nmol K16ApoE peptide. Brain Fluc activity was measured three weeks post-injection. Fold enhancement with K16ApoE peptide was calculated for each AAV vector and shown above the respective pairs of bars. Data is represented as the mean±standard deviation. FIG. 6 shows co-injection of K16ApoE enhances CNS gene transfer of different recombinant AAV vectors, such as AAV9, AAVrh.10, AAV9.45-AS, and AAV9.45-Angiopep.

---

Sequences

>AAV1

(SEQ ID NO: 1)

MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAKKR

LNFGQTGDSESVPDPQPLGEPPATPAAVGPTTMASGGGAPMADNNEGADGVGNASGN

Sequences

WHCDSTWLGDRVITTSTRTWALPTYNNHLYKQISSASTGASNDNHYFGYSTPWGYFDF

NRFHCHFSPRDWQRLINNNWGFRPKRLNFKLFNIQVKEVTTNDGVTTIANNLTSTVQVF

SDSEYQLPYVLGSAHQGCLPPFPADVFMIPQYGYLTLNNGSQAVGRSSFYCLEYFPSQM

LRTGNNFTFSYTFEEVPFHSSYAHSQSLDRLMNPLIDQYLYYLNRTQNQSGSAQNKDLL

FSRGSPAGMSVQPKNWLPGPCYRQQRVSKTKTDNNNSNFTWTGASKYNLNGRESIINP

GTAMASHKDDEDKFFPMSGVMIFGKESAGASNTALDNVMITDEEEIKATNPVATERFG

TVAVNFQSSSTDPATGDVHAMGALPGMVWQDRDVYLQGPIWAKIPHTDGHFHPSPLM

GGFGLKNPPPQILIKNTPVPANPPAEFSATKFASFITQYSTGQVSVEIEWELQKENSKRW

NPEVQYTSNYAKSANVDFTVDNNGLYTEPRPIGTRYLTRPL

>AAV2
                                                                    (SEQ ID NO: 2)
MAADGYLPDWLEDTLSEGIRQWWKLKPGPPPPKPAERHKDDSRGLVLPGYKYLGPFN

GLDKGEPVNEADAAALEHDKAYDRQLDSGDNPYLKYNHADAEFQERLKEDTSFGGNL

GRAVFQAKKRVLEPLGLVEEPVKTAPGKKRPVEHSPVEPDSSSGTGKAGQQPARKRLN

FGQTGDADSVPDPQPLGQPPAAPSGLGTNTMATGSGAPMADNNEGADGVGNSSGNWH

CDSTWMGDRVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLR

TGNNFTFSYTFEDVPFHSSYAHSQSLDRLMNPLIDQYLYYLSRTNTPSGTTTQSRLQFSQ

AGASDIRDQSRNWLPGPCYRQQRVSKTSADNNNSEYSWTGATKYHLNGRDSLVNPGP

AMASHKDDEEKFFPQSGVLIFGKQGSEKTNVDIEKVMITDEEEIRTTNPVATEQYGSVST

NLQRGNRQAATADVNTQGVLPGMVWQDRDVYLQGPIWAKIPHTDGHFHPSPLMGGF

GLKHPPPQILIKNTPVPANPSTTFSAAKFASFITQYSTGQVSVEIEWELQKENSKRWNPEI

QYTSNYNKSVNVDFTVDTNGVYSEPRPIGTRFLTRNL

>AAV2i8
                                                                    (SEQ ID NO: 3)
MAADGYLPDWLEDTLSEGIRQWWKLKPGPPPPKPAERHKDDSRGLVLPGYKYLGPFN

GLDKGEPVNEADAAALEHDKAYDRQLDSGDNPYLKYNHADAEFQERLKEDTSFGGNL

GRAVFQAKKRVLEPLGLVEEPVKTAPGKKRPVEHSPVEPDSSSGTGKAGQQPARKRLN

FGQTGDADSVPDPQPLGQPPAAPSGLGTNTMATGSGAPMADNNEGADGVGNSSGNWH

CDSTWMGDRVITTSTRTWALPTYNNHLYKQISSQSGASNDNHYFGYSTPWGYFDFNRF

HCHFSPRDWQRLINNNWGFRPKRLNFKLFNIQVKEVTQNDGTTTIANNLTSTVQVFTDS

EYQLPYVLGSAHQGCLPPFPADVFMVPQYGYLTLNNGSQAVGRSSFYCLEYFPSQMLR

TGNNFTFSYTFEDVPFHSSYAHSQSLDRLMNPLIDQYLYYLSRTNTPSGTTTQSRLQFSQ

AGASDIRDQSRNWLPGPCYRQQRVSKTSADNNNSEYSWTGATKYHLNGRDSLVNPGP

AMASHKDDEEKFFPQSGVLIFGKQGSEKTNVDIEKVMITDEEEIRTTNPVATEQYGSVST

NLQQQNTAPATADVNTQGVLPGMVWQDRDVYLQGPIWAKIPHTDGHFHPSPLMGGFG

LKHPPPQILIKNTPVPANPSTTFSAAKFASFITQYSTGQVSVEIEWELQKENSKRWNPEIQ

YTSNYNKSVNVDFTVDTNGVYSEPRPIGTRFLTRNL

-continued

| Sequences |
| --- |

>AAV2.5

(SEQ ID NO: 4)

MAADGYLPDWLEDTLSEGIRQWWKLKPGPPPPKPAERHKDDSRGLVLPGYKYLGPFN

GLDKGEPVNEADAAALEHDKAYDRQLDSGDNPYLKYNHADAEFQERLKEDTSFGGNL

GRAVFQAKKRVLEPLGLVEEPVKTAPGKKRPVEHSPVEPDSSSGTGKAGQQPARKRLN

FGQTGDADSVPDPQPLGQPPAAPSGLGTNTMATGSGAPMADNNEGADGVGNSSGNWH

CDSTWMGDRVITTSTRTWALPTYNNHLYKQISSASTGASNDNHYFGYSTPWGYFDFNR

FHCHFSPRDWQRLINNNWGFRPKRLNFKLFNIQVKEVTQNDGTTTIANNLTSTVQVFTD

SEYQLPYVLGSAHQGCLPPFPADVFMVPQYGYLTLNNGSQAVGRSSFYCLEYFPSQML

RTGNNFTFSYTFEDVPFHSSYAHSQSLDRLMNPLIDQYLYYLSRTNTPSGTTTQSRLQFS

QAGASDIRDQSRNWLPGPCYRQQRVSKTSADNNNSEYSWTGATKYHLNGRDSLVNPG

PAMASHKDDEEKFFPQSGVLIFGKQGSEKTNVDIEKVMITDEEEIRTTNPVATEQYGSVS

TNLQRGNRQAATADVNTQGVLPGMVWQDRDVYLQGPIWAKIPHTDGHFHPSPLMGGF

GLKHPPPQILIKNTPVPANPSTTFSAAKFASFITQYSTGQVSVEIEWELQKENSKRWNPEI

QYTSNYAKSANVDFTVDNNGVYSEPRPIGTRFLTRNL

>AAV6

(SEQ ID NO: 5)

MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPFGLVEEGAKTAPGKKRPVEQSPQEPDSSSGIGKTGQQPAKKRL

NFGQTGDSESVPDPQPLGEPPATPAAVGPTTMASGGGAPMADNNEGADGVGNASGNW

HCDSTWLGDRVITTSTRTWALPTYNNHLYKQISSASTGASNDNHYFGYSTPWGYFDFN

RFHCHFSPRDWQRLINNNWGFRPKRLNFKLFNIQVKEVTTNDGVTTIANNLTSTVQVFS

DSEYQLPYVLGSAHQGCLPPFPADVFMIPQYGYLTLNNGSQAVGRSSFYCLEYFPSQML

RTGNNFTFSYTFEDVPFHSSYAHSQSLDRLMNPLIDQYLYYLNRTQNQSGSAQNKDLLF

SRGSPAGMSVQPKNWLPGPCYRQQRVSKTKTDNNNSNFTWTGASKYNLNGRESIINPG

TAMASHKDDKDKFFPMSGVMIFGKESAGASNTALDNVMITDEEEIKATNPVATERFGT

VAVNLQSSSTDPATGDVHVMGALPGMVWQDRDVYLQGPIWAKIPHTDGHFHPSPLMG

GFGLKHPPPQILIKNTPVPANPPAEFSATKFASFITQYSTGQVSVEIEWELQKENSKRWNP

EVQYTSNYAKSANVDFTVDNNGLYTEPRPIGTRYLTRPL

>AAV8

(SEQ ID NO: 6)

MAADGYLPDWLEDNLSEGIREWWALKPGAPKPKANQQKQDDGRGLVLPGYKYLGPF

NGLDKGEPVNAADAAALEHDKAYDQQLQAGDNPYLRYNHADAEFQERLQEDTSFGG

NLGRAVFQAKKRVLEPLGLVEEGAKTAPGKKRPVEPSPQRSPDSSTGIGKKGQQPARKR

LNFGQTGDSESVPDPQPLGEPPAAPSGVGPNTMAAGGGAPMADNNEGADGVGSSSGN

WHCDSTWLGDRVITTSTRTWALPTYNNHLYKQISNGTSGGATNDNTYFGYSTPWGYF

DFNRFHCHFSPRDWQRLINNNWGFRPKRLSFKLFNIQVKEVTQNEGTKTIANNLTSTIQ

VFTDSEYQLPYVLGSAHQGCLPPFPADVFMIPQYGYLTLNNGSQAVGRSSFYCLEYFPS

QMLRTGNNFQFTYTFEDVPFHSSYAHSQSLDRLMNPLIDQYLYYLSRTQTTGGTANTQT

LGFSQGGPNTMANQAKNWLPGPCYRQQRVSTTTGQNNNSNFAWTAGTKYHLNGRNS

Sequences

LANPGIAMATHKDDEERFFPSNGILIFGKQNAARDNADYSDVMLTSEEEIKTTNPVATE

EYGIVADNLQQQNTAPQIGTVNSQGALPGMVWQNRDVYLQGPIWAKIPHTDGNFHPSP

LMGGFGLKHPPPQILIKNTPVPADPPTTFNQSKLNSFITQYSTGQVSVEIEWELQKENSKR

WNPEIQYTSNYYKSTSVDFAVNTEGVYSEPRPIGTRYLTRNL

>AAVrh8
(SEQ ID NO: 7)
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEQSPQEPDSSSGIGKTGQQPAKKR

LNFGQTGDSESVPDPQPLGEPPAAPSGLGPNTMASGGGAPMADNNEGADGVGNSSGN

WHCDSTWLGDRVITTSTRTWALPTYNNHLYKQISNGTSGGSTNDNTYFGYSTPWGYFD

FNRFHCHFSPRDWQRLINNNWGFRPKRLNFKLFNIQVKEVTTNEGTKTIANNLTSTVQV

FTDSEYQLPYVLGSAHQGCLPPFPADVFMVPQYGYLTLNNGSQALGRSSFYCLEYFPSQ

MLRTGNNFQFSYTFEDVPFHSSYAHSQSLDRLMNPLIDQYLYYLVRTQTTGTGGTQTLA

FSQAGPSSMANQARNWVPGPCYRQQRVSTTTNQNNNSNFAWTGAAKFKLNGRDSLM

NPGVAMASHKDDDDRFFPSSGVLIFGKQGAGNDGVDYSQVLITDEEEIKATNPVATEEY

GAVAINNQAANTQAQTGLVHNQGVIPGMVWQNRDVYLQGPIWAKIPHTDGNFHPSPL

MGGFGLKHPPPQILIKNTPVPADPPLTFNQAKLNSFITQYSTGQVSVEIEWELQKENSKR

WNPEIQYTSNYYKSTNVDFAVNTEGVYSEPRPIGTRYLTRNL

>AAV9
(SEQ ID NO: 8)
MAADGYLPDWLEDNLSEGIREWWALKPGAPQPKANQQHQDNARGLVLPGYKYLGPG

NGLDKGEPVNAADAAALEHDKAYDQQLKAGDNPYLKYNHADAEFQERLKEDTSFGG

NLGRAVFQAKKRLLEPLGLVEEAAKTAPGKKRPVEQSPQEPDSSAGIGKSGAQPAKKR

LNFGQTGDTESVPDPQPIGEPPAAPSGVGSLTMASGGGAPVADNNEGADGVGSSSGNW

HCDSQWLGDRVITTSTRTWALPTYNNHLYKQISNSTSGGSSNDNAYFGYSTPWGYFDF

NRFHCHFSPRDWQRLINNNWGFRPKRLNFKLFNIQVKEVTDNNGVKTIANNLTSTVQV

FTDSDYQLPYVLGSAHEGCLPPFPADVFMIPQYGYLTLNDGSQAVGRSSFYCLEYFPSQ

MLRTGNNFQFSYEFENVPFHSSYAHSQSLDRLMNPLIDQYLYYLSKTINGSGQNQQTLK

FSVAGPSNMAVQGRNYIPGPSYRQQRVSTTVTQNNNSEFAWPGASSWALNGRNSLMN

PGPAMASHKEGEDRFFPLSGSLIFGKQGTGRDNVDADKVMITNEEEIKTTNPVATESYG

QVATNHQSAQAQAQTGWVQNQGILPGMVWQDRDVYLQGPIWAKIPHTDGNFHPSPL

MGGFGMKHPPPQILIKNTPVPADPPTAFNKDKLNSFITQYSTGQVSVEIEWELQKENSKR

WNPEIQYTSNYYKSNNVEFAVNTEGVYSEPRPIGTRYLTRNL

>AAVrh10
(SEQ ID NO: 9)
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADAEFQERLQEDTSFGG

NLGRAVFQAKKRVLEPLGLVEEGAKTAPGKKRPVEPSPQRSPDSSTGIGKKGQQPAKK

RLNFGQTGDSESVPDPQPIGEPPAGPSGLGSGTMAAGGGAPMADNNEGADGVGNSSGN

WHCDSTWLGDRVITTSTRTWALPTYNNHLYKQISNGTSGGSTNDNTYFGYSTPWGYFD

FNRFHCHFSPRDWQRLINNNWGFRPKRLNFKLFNIQVKEVTQNEGTKTIANNLTSTIQV

-continued

Sequences

FTDSEYQLPYVLGSAHQGCLPPFPADVFMIPQYGYLTLNNGSQAVGRSSFYCLEYFPSQ

MLRTGNNFEFSYQFEDVPFHSSYAHSQSLDRLMNPLIDQYLYYLSRTQSTGGTAGTQQL

LFSQAGPNNMSAQAKNWLPGPCYRQQRVSTTLSQNNNSNFAWTGATKYHLNGRDSLV

NPGVAMATHKDDEERFFPSSGVLMFGKQGAGKDNVDYSSVMLTSEEEIKTTNPVATEQ

YGVVADNLQQQNAAPIVGAVNSQGALPGMVWQNRDVYLQGPIWAKIPHTDGNFHPSP

LMGGFGLKHPPPQILIKNTPVPADPPTTFSQAKLASFITQYSTGQVSVEIEWELQKENSKR

WNPEIQYTSNYYKSTNVDFAVNTDGTYSEPRPIGTRYLTRNL

>AAV-B1
(SEQ ID NO: 10)
MAADGYLPDWLEDNLSEGIREWWDLKPGAPKPKANQQKQDDGRGLVLPGYKYLGPF

NGLDKGEPVNAADAAALEHDKAYDQQLKAGDNPYLRYNHADVEFQERLQEDTSFGG

NLGRAVFQAKKRVLEPFGLVEEGAKTAPGKKRPVEQSPQEPDSSSGIGKKGQQPARKR

LNFGQTGDSESVPDPQPLGEPPAAPSGVGPNTMAAGGGAPMADNNEGADGVGNSSGN

WHCDSTWMGDRVITTSTRTWALPTYNNHLYKQISNGTSGGSTNDNTYFGYSTPWGYF

DFNRFHCHFSPRDWQRLINNNWGFRPKRLSFKLFNIQVKEVTQNEGTKTIANNLTSTIQ

VFTDSEYQLPYVLGSAHQGCLPPFPADVFMIPQYGYLTLNNGSQAVGRSSFYCLEYFPS

QMLRTGNNFEFSYQFEDVPFHSSYAHSQSLDRLMNPLIDQYLYYLSRTQSTGGTARTQQ

LLFSQAGPNTMANQAKNWLPGPCYRQQRVSTTTGQNNNSNSAWTAGTKYHLNGRNS

LANPGIAMATHKDDEERFFPSNGILIFGKQNAARDNADYSDVMLTSEEEIKTTNPVATE

EYGIVADNLQQQNTAPQIGTVNSQGALPGMVWQNRDVYLQGPIWAKIPHTDGNFHPSP

LMGGFGLKHPPPQILIKNTPVPADPPTTFNQSKLNSFITQYSTGQVSVEIEWELQKENSKR

WNPEIQYTSNYYKSTSVDFAVNTEGVYSEPRPIGTRYLTRNL

>AAV9.45VP2A-String
(SEQ ID NO: 11)
MAAAAAAAAAAAAAAAAAAAAAGGGGSAPGKKRPVEQSPQEPDSSAGIGKSGAQPAKK

RLNFGQTGDTESVPDPQPIGEPPAAPSGVGSLTMASGGGAPVADNNEGADGVGSSSGN

WHCDSQWLGDRVITTSTRTWALPTYNNHLYKQISNSTSGGSSNDNAYFGYSTPWGYFD

FNRFHCHFSPRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRSSFYCLEYFPS

QMLRTGNNFQFSYEFENVPFHSSYAHSQSLDRLMNPLIDQYLYYLSKTINGSGQNQQTL

KFSVAGPSNMAVQGRNYIPGPSYRQQRVSTTVTQNNYSEFAWPGASSWALNGRNSLM

NPGPAMASHKEGEDRFFPLSGSLIFGKQGTGRDNVDADKVMITNEEEIKTTNPVATESY

GQVATNHQSAQAQAQTGWVQNQGIFPGMVWQDRDVYLQGPIWAKIPHTDGNFHPSPL

MGGFGMKHPPPQILIKNTPVPADPPTAFNKDKLNSFITQYSTGQVSVEIEWELQKENSKR

WNPEIQYTSNYYKSNNVEFAVNTEGVYSEPRPIGTRYLTRNL

>AAV9.45VP2Angiopep-2
(SEQ ID NO: 12)
MTFFYGGSRGKRNNFKTEEYGGGGSAPGKKRPVEQSPQEPDSSAGIGKSGAQPAKKRL

NFGQTGDTESVPDPQPIGEPPAAPSGVGSLTMASGGGAPVADNNEGADGVGSSSGNWH

CDSQWLGDRVITTSTRTWALPTYNNHLYKQISNSTSGGSSNDNAYFGYSTPWGYFDFN

RFHCHFSPRDWQRLINNNWGFRPKRLNFKLFNIQVKEVTDNNGVKTIANNLTSTVQVFT

-continued

| Sequences |
| --- |

DSDYQLPYVLGSAHEGCLPPFPADVFMIPQYGYLTLNDGSQAVGRSSFYCLEYFPSQML

RTGNNFQFSYEFENVPFHSSYAHSQSLDRLMNPLIDQYLYYLSKTINGSGQNQQTLKFS

VAGPSNMAVQGRNYIPGPSYRQQRVSTTVTQNNYSEFAWPGASSWALNGRNSLMNPG

PAMASHKEGEDRFFPLSGSLIFGKQGTGRDNVDADKVMITNEEEIKTTNPVATESYGQV

ATNHQSAQAQAQTGWVQNQGIFPGMVWQDRDVYLQGPIWAKIPHTDGNFHPSPLMG

GFGMKHPPPQILIKNTPVPADPPTAFNKDKLNSFITQYSTGQVSVEIEWELQKENSKRWN

PEIQYTSNYYKSNNVEFAVNTEGVYSEPRPIGTRYLTRNL

>AAV9.47VP2Angiopep-2

(SEQ ID NO: 13)
MTFFYGGSRGKRNNFKTEEYGGGGSAPGKKRPVEQSPQEPDSSAGIGKSGAQPAKKRL

NFGQTGDTESVPDPQPIGEPPAAPSGVGSLTMASGGGAPVADNNEGADGVGSSSGNWH

CDSQWLGDRVITTSTRTWALPTYNNHLYKQISNSTSGGSSNDNAYFGYSTPWGYFDFN

RFHCHFSPRDWQRLINNNWGFRPKRLNFKLFNIQVKEVTDNNGVKTIANNLTSTVQVFT

DSDYQLPYVLGSAHEGCLPPFPADVFMIPQYGYLTLNDGSQAVGRSSFYCLEYFPSQML

RTGNNFQFNYEFENVPFHSSYAHSQSLDRLMNPLIDQYLYYLSKTINDSGQNQQTLKFS

VAGPSNMAVQGRNYIPGPSYRQQRVSTTVTQNNNSEFAWPGASSWALNGRNSLMNPG

PAMASHKEGEDRFFPLSGSLIFGKQGTGRDNVDADEVMITNEEEIKTTNPVATESYGQV

AINHQSAQAQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWELQKENSKRWNP

EIQYTSNYYKSNNVEFAVNTEGVYSEPRPIGTRYLTRNL*

>AAV9.47VP2A-string (SEQ ID NO: 14)
MAAAAAAAAAAAAAAAAAAAAGGGGSAPGKKRPVEQSPQEPDSSAGIGKSGAQPAKK

RLNFGQTGDTESVPDPQPIGEPPAAPSGVGSLTMASGGGAPVADNNEGADGVGSSSGN

WHCDSQWLGDRVITTSTRTWALPTYNNHLYKQISNSTSGGSSNDNAYFGYSTPWGYFD

FNRFHCHFSPRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRSSFYCLEYFPS

QMLRTGNNFQFNYEFENVPFHSSYAHSQSLDRLMNPLIDQYLYYLSKTINDSGQNQQTL

KFSVAGPSNMAVQGRNYIPGPSYRQQRVSTTVTQNNNSEFAWPGASSWALNGRNSLM

NPGPAMASHKEGEDRFFPLSGSLIFGKQGTGRDNVDADEVMITNEEEIKTTNPVATESY

GQVAINHQSAQAQAQTGWVQNQGILPGMVWQDRDVYLQGPIWAKIPHTDGNFHPSPL

MGGFGMKHPPPQILIKNTPVPADPPTAFNKDKLNSFITQYSTGQVSVEIEWELQKENSKR

WNPEIQYTSNYYKSNNVEFAVNTEGVYSEPRPIGTRYLTRNL*

>Angiopep2

(SEQ ID NO: 15)
TFFYGGSRGKRNNFKTEEY

>A-String (SEQ ID NO: 16)
AAAAAAAAAAAAAAAAAAAA

>K16ApoE (SEQ ID NO: 17)
KKKKKKKKKKKKKKKKLRVRLASHLRKLRKRLLRDA

>K4

(SEQ ID NO: 18)
KKKK

-continued

---
Sequences
---

>K8
                                                        (SEQ ID NO: 19)
KKKKKKKK

>K12
                                                        (SEQ ID NO: 20)
KKKKKKKKKKKK

>K16
                                                        (SEQ ID NO: 21)
KKKKKKKKKKKKKKKK

>K20
                                                        (SEQ ID NO: 22)
KKKKKKKKKKKKKKKKKKKK

>ApoE
                                                        (SEQ ID NO: 23)
LRVRLASHLRKLRKRLLRD

---

What is claimed is:

1. A method for delivering a transgene to CNS tissue in a subject, the method comprising co-administering to the subject:

(i) an effective amount of a targeting composition, wherein the targeting composition comprises a hydrophilic peptide comprising the amino acid sequence of SEQ ID NO: 17; and, (ii) an effective amount of a recombinant adeno-associated virus (rAAV) comprising a nucleic acid comprising a promoter operably linked to a transgene and a capsid protein comprising an N-terminally grafted heterologous targeting peptide comprises or consists of a sequence selected from the group consisting of SEQ ID NOS: 15-17; wherein the co-administering comprises systemic co-injection.

2. The method of claim 1, wherein the capsid protein has a serotype selected from the group consisting of AAV1, AAV2, AAV2i8, AAV2.5, AAV6, AAV8, AAVrh8, AAV9, AAVrh10, AAV-B1, AAV9.45A-String, AAV9.45Angiopep, AAV9.47-Angiopep, and AAV9.47-AS.

3. The method of claim 1, wherein the capsid protein comprises or consists of a sequence selected from the group consisting of SEQ ID NOS: 10-14.

4. The method of claim 1, wherein the N-terminally grafted heterologous targeting peptide is expressed on the surface of the rAAV.

5. The method of claim 1, wherein the capsid protein is a VP2 capsid protein.

6. The method of claim 1, wherein the transgene is a CNS-associated transgene selected from the group consisting of ALS2, ANG, ATXN2, C9orf72, DCTN1, FIG. 4, FUS, NEFH, OPTN, PFN1, PRPH, SETX, SIGMAR1, SMN1, SOD1, SPG11, TARDBP, UBQLN2, VAPB, VCP, Htt, Xbpls, CRAG, MAN2B1, MAN2B2, MAN2C1, AGA, CLN1, CLN2, CLN3, CLN5, CLN6, MFSD8, CLN8, CTSD, MANBA, CTNS, LAMP2, GLA, ASAH1, FUCA1, CTSA, GBA, GALC, GLB1, HEXA, HEXB, ARSA, IDUA, IDS, SGSH, NAGLU, HGSNAT, GNS, GALNS, ARSB, GUSB, HYAL1, SMPD1, NPC1, NPC2, GAA, NAGA, SLCA17A5, and LAL.

*     *     *     *     *